United States Patent
Cigan et al.

(10) Patent No.: US 11,827,894 B2
(45) Date of Patent: *Nov. 28, 2023

(54) WAXY CORN

(71) Applicant: PIONEER HI-BRED INTERNATIONAL, INC., Johnston, IA (US)

(72) Inventors: Andrew Mark Cigan, Madison, WI (US); Mark Jacob Gadlage, Dyersburg, TN (US); Huirong Gao, Johnston, IA (US); Robert B Meeley, Des Moines, IA (US); Joshua K Young, Johnston, IA (US)

(73) Assignee: PIONEER HI-BRED INTERNATIONAL, INC

( * ) Notice: Subject to any disclaimer, the term of this patent is extended or adjusted under 35 U.S.C. 154(b) by 0 days.

This patent is subject to a terminal disclaimer.

(21) Appl. No.: 17/465,199

(22) Filed: Sep. 2, 2021

(65) Prior Publication Data

US 2022/0162628 A1 May 26, 2022

Related U.S. Application Data

(63) Continuation of application No. 16/072,706, filed as application No. PCT/US2017/014903 on Jan. 25, 2017, now Pat. No. 11,136,589.

(60) Provisional application No. 62/287,115, filed on Jan. 26, 2016.

(51) Int. Cl.
*C12N 15/82* (2006.01)
*A01H 5/10* (2018.01)
*C12N 9/10* (2006.01)
*A01H 6/46* (2018.01)

(52) U.S. Cl.
CPC .......... *C12N 15/8245* (2013.01); *A01H 5/10* (2013.01); *A01H 6/4684* (2018.05); *C12N 9/1051* (2013.01); *C12N 15/8213* (2013.01); *C12N 2310/20* (2017.05)

(58) Field of Classification Search
CPC .................................................. C12N 15/82
See application file for complete search history.

(56) References Cited

U.S. PATENT DOCUMENTS

| | | | | |
|---|---|---|---|---|
| 8,252,975 B2 * | 8/2012 | Frohberg | ........... | C12N 15/8245 435/468 |
| 11,136,589 B2 * | 10/2021 | Cigan | ..................... | A01H 5/10 |
| 2013/0115362 A1 * | 5/2013 | Regina | ........... | C12Y 204/01018 536/102 |

FOREIGN PATENT DOCUMENTS

| | | |
|---|---|---|
| EP | 1428885 A1 | 6/2004 |
| WO | 2014104878 A1 | 7/2014 |
| WO | 2015/193858 A1 | 12/2015 |

OTHER PUBLICATIONS

Terada et al (2002 Nature Biotechnology 20:1030-1034 (Year: 2002) provided by Applicant.*
Xingliang et al (2015 Molecular Plant 8:1274-1284 (Year: 2015) provided by APPLICANT.*
Cook et al (2012 Plant Physiology 158:824-834 (Year: 2012) provided by Applicant.*
Yandeau-Nelson et al (2006 Genetics 174:101-112 (Year: 2006) provided by Applicant.*
Nishizawa-Yokoi, Ayako, et al: "A Defect in DNA Ligase4 Enhances the Frequency of TALEN-Mediated Targeted Mutagenesis in Rice", Plant Physiology, Dec. 14, 2015, vol. 170, No. 2, pp. 653-666.
Hohn, Barbara, et al: "Some like it sticky: Targeting of the rice gene Waxy.", Trends in Plance Science, Feb. 2003, vol. 8, No. 2, pp. 51-53.
Ozawa, K., et al: "Development of an Efficient Agrobacterium-Mediated Gene Targeting System for Rice and Analysis of Rice Knockouts Lacking Granule-Bound Starch Synthase (Waxy) and 1, 2-Xylosyltransferase", Plant and Cell Physiology, Feb. 10, 2012, vol. 53, No. 4, pp. 755-761.
Lieng, Zhen, et al: Targeted Mutagenesis in *Zea mays* Using Talens and the CRISPR/Cas System, Journal of Genetics and Genomics, Dec. 14, 2013, vol. 41, No. 2, pp. 63-68.
Svitashev, Sergei, et al: "Targeted Mutagenesis, Precise Gene Editing, and Site-Specific Gene Insertion in Maize Using Cas9 and Guide RNA", Plant Physiology, Aug. 28, 2015, vol. 169, No. 2, pp. 931-945.
Svitashev, Sergei, et al: "Genome editing in maize directed by CRISPR-Cas9 ribonucleoprotein complexes", Naure Communications, Nov. 16, 2016, vol. 7, p. 13274.
Terada, Rie, et al: "Cre-loxP mediated marker elimination and gene reactivation at the waxy locus created in rice genome based on strong positive-negative selection", Plant Biotechnology, 2010, vol. 27, No. 1, pp. 29-37.
Shukla, Vipula K., et al: "Precise genome modification in the crop species *Zea mays* using zinc-finger nucleases", Nature, May 21, 2009, vol. 459, No. 7245, p. 437.
International Search Report and Written Opinion, International Application No. PCT/US2017/014903 dated Oct. 4, 2017.
Terada, et al (2002) Nature Biotechnology 20:1030-1034.
Xingliang, et al (2015) Molecular Plant 8:1274-1284.
Cook, et al (2012) Plant Physiology 158:824-834.
Yandeau-Nelson, et al (2006) Genetics 174:101-112.
Maize Genome Database Definition of Deletion Oct. 2006 maizegdb.org/nomenclature.

* cited by examiner

*Primary Examiner* — Brent T Page

(57) ABSTRACT

The present disclosure involves the production of Waxy maize. Compositions and methods are provided for knocking out expression of the Waxy (Wx1) gene in maize by making double strand breaks at one or more target sites in an endogenous WX1 encoding sequence. Some methods employ one or more guide polynucleotides and a Cas endonuclease, wherein Cas endonuclease is guided by the one or more guide polynucleotides to recognize and introduce double strand breaks at specific target sites in and around the Wx1 gene. Also provided are compositions and methods for the production of Waxy maize plant cells, plant explants, seeds and grain.

12 Claims, 6 Drawing Sheets

Figures 1A, 1B:
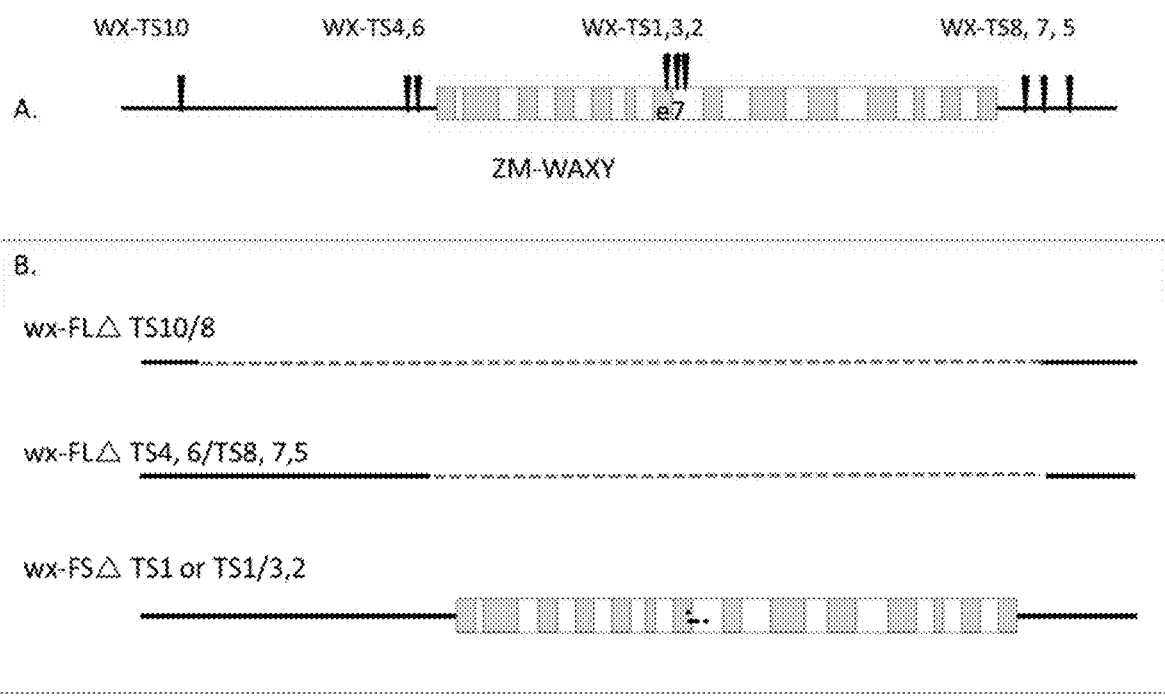

Specification includes a Sequence Listing.

```
SEQ
ID                    WX-TS1                                              WX-TS3
NO:                     ↓                                                   ↓
68   TCCCACGGCATCTACAGGGACGCAAAG GTTGCCTTCTCTGAACTGAACAACG CCG CTTCGTTCTCCATGCT
69   TCCCACGGCATCTACAGGGACGC::::::::::::::::::::::::::::::CGTCTTCGTTCTCCATGCT
70   TCCCACGGCATCTACAGGGAC:CAAAGGTTGCCTTCTCTGAACTGAACAACGCCGTCTTCGTTCTCCATGCT
71   TCCCACGGCATCTACAGGGACG:AAAGGTTGCCTTCTCTGAACTGAACAACGCCGTCTTCGTTCTCCATGCT
72   TCCCACGGCATCTACAGGGA::CAAAGGTTGCCTTCTCTGAACTGAACAACGCCGTCTTCGTTCTCCATGCT
73   TCCCACGGCATCT::::::::GCAAAGGTTGCCTTCTCTGAACTGAACAACGCCGTCTTCGTTCTCCATGCT
74   TCCCACGGCAT::::::::::GCAAAGGTTGCCTTCTCTGAACTGAACAACGCCGTCTTCGTTCTCCATGCT
75   TCCCACGGCATCTACAGGGACG::::::::::::::::::::::::::::::::::TCGTTCTCCATGCT
76   TCCCACGGCATCTACAG:::::::::::TGCCTTCTCTGAACTGAACAACGCCGTCTTCGTTCTCCATGCT
```

Fig. 5

A. Pollen

B. Waxy kernel

Whole waxy deletion

F2: 30bp deletion

SEQUENCE LISTING

<160> NUMBER OF SEQ ID NOS: 76

<210> SEQ ID NO 1
<211> LENGTH: 20
<212> TYPE: DNA
<213> ORGANISM: Zea mays

<400> SEQUENCE: 1
gcccaaaacg ctttcccgat        20

<210> SEQ ID NO 2
<211> LENGTH: 19
<212> TYPE: DNA
<213> ORGANISM: Zea mays

<400> SEQUENCE: 2

-continued gcaatataaa attaccgat                                        19

<210> SEQ ID NO 3
<211> LENGTH: 21
<212> TYPE: DNA
<213> ORGANISM: Zea mays

<400> SEQUENCE: 3
gctgggagag acggtgtagt a                                     21

<210> SEQ ID NO 4
<211> LENGTH: 19
<212> TYPE: DNA
<213> ORGANISM: Zea mays

<400> SEQUENCE: 4
ggcatctaca gggacgcaa                                        19

<210> SEQ ID NO 5
<211> LENGTH: 18
<212> TYPE: DNA
<213> ORGANISM: Zea mays

<400> SEQUENCE: 5
gagcatggag aacgaaaa                                         18

<210> SEQ ID NO 6
<211> LENGTH: 18
<212> TYPE: DNA
<213> ORGANISM: Zea mays

<400> SEQUENCE: 6
gctcgtatat acctcgtc                                         18

<210> SEQ ID NO 7
<211> LENGTH: 18
<212> TYPE: DNA
<213> ORGANISM: Zea mays

<400> SEQUENCE: 7
gctggtgcgc agtgccgg                                         18

<210> SEQ ID NO 8
<211> LENGTH: 21
<212> TYPE: DNA
<213> ORGANISM: Zea mays

<400> SEQUENCE: 8
gacaatgccc taaatatcta t                                     21

<210> SEQ ID NO 9
<211> LENGTH: 18
<212> TYPE: DNA
<213> ORGANISM: Zea mays

<400> SEQUENCE: 9
gagaccatag cctatctt                                         18

<210> SEQ ID NO 10
<211> LENGTH: 4296
<212> TYPE: DNA
<213> ORGANISM: Artificial
<220> FEATURE:

<223> OTHER INFORMATION: mCas9 gene(mod2) with ST-L1 intron2

<400> SEQUENCE: 10

```
atggataaga agtacagcat cggcctcgac atcgggacca acagcgtcgg ctgggccgtc      60
atcaccgacg aatataaggt gcccagcaag aagttcaagg tgctcgggaa tacagaccgc     120
cacagcatca agaagaacct gatcggcgcc ctcctgttcg actcgggcga gaccgctgag     180
gccaccagac taaagaggac cgctcgccgc cgctacaccc gccgcaagaa ccgcatatgc     240
tacctccagg agatcttcag caacgagatg gccaaggtgg acgacagctt cttccaccgc     300
cttgaggagt cgttcctcgt ggaggaggac aagaagcatg agaggcaccc gatcttcggg     360
aacatcgtgg acgaggtaag tttctgcttc tacctttgat atatatataa taattatcat     420
taattagtag taatataata tttcaaatat ttttttcaaa ataaaagaat gtagtatata     480
gcaattgctt ttctgtagtt tataagtgtg tatatttttaa tttataactt ttctaatata    540
tgaccaaaac atggtgatgt gcaggtggcg taccacgaga agtacccgac gatctaccac     600
ctccgcaaga agctggtcga ctccacagac aaggccgacc tcagactgat ctacctggcc     660
ctcgcgcaca tgatcaagtt ccgcgggcac ttcctcatcg agggcgacct gaacccggac     720
aactccgacg tcgacaagct cttcatccag ctggtccaga cctacaatca actgttcgag     780
gagaacccga tcaacgcgtc cggcgtggac gcgaaggcca tcctcagcgc gaggctcagc     840
aaaatcaaga cggctggaga acctgatcgc cagctcccag gcgagaagaa aaacggcttg     900
ttcggcaacc tgatcgcgct ctcgctcggc ctcacgccca acttcaaatc aaacttcgac     960
ctggccgaga cgcgaaact gcagctgtcc aaggacactt acgacgacga cctcgacaac    1020
ctgctggcgc aaatcggtga ccagtacgca gacctcttcc tggccgccaa gaacctctcg    1080
gacgccatcc tgctgtccga tatcctgaga gtgaatacgg agatcaccaa ggcgccgctc    1140
agcgcctcca tgattaaaag gtacgacgag caccaccagg acctgacgct gctcaaggcc    1200
ctggtgcgcc agcagctccc cgagaagtac aaggagatct tcttcgacca atcaaaaaac    1260
ggctacgccg gctacatcga cggggggcgcc tcccaggagg agttctacaa gttcatcaaa    1320
ccaattctcg agaagatgga cggcacggag gagcttctcg tgaagctcaa ccgggaggac    1380
ctcctgagga agcagaggac gttcgacaac ggctcgatac cgcatcagat ccacctgggc    1440
gagctccacg ccatcctgcg ccggcaggag gatttctatc cgttcctcaa ggacaacagg    1500
gagaagatcg agaaaattct gacgttccgc atcccgtact acgtgggccc tctcgcgcgc    1560
gggaacagcc ggttcgcctg gatgactcgg aagtcggagg agacgatcac gccgtggaac    1620
ttcgaggagg tggtggacaa gggcgcctcc gcccagtcgt tcatcgagcg catgacgaac    1680
ttcgataaaa atctgcccaa tgaaaaagtg ctcccgaagc acagcctcct ctacgagtac    1740
ttcacggtgt acaacgagct cacgaaggtg aagtacgtga ccgagggtat gcggaagccg    1800
gcgttcctga cggcgagca agaagaaggcc atcgtggacc tcctcttcaa gacgaaccgg    1860
aaagtcaccg tgaagcaatt aaaggaggac tacttcaaga aaatagagtg cttcgacagc    1920
gtcgagatct cgggcgtcga ggacaggttc aacgcgtcgc tgggcacata ccacgacctc    1980
ctcaagatca ttaaagacaa ggacttcctg gacaacgagg agaacgagga catcctcgag    2040
gacatcgtgc tgaccctcac cctgtttgag gaccgggaga tgatcgagga cgcgctcaag    2100
acgtacgctc accttttcga cgacaaggtg atgaaacagc tgaagcggcg ccgctacacc    2160
ggatggggcc ggctctcccg caagctcatt aatgggatca gggacaagca gtccggcaag    2220
accatactcg atttcctgaa gagcgacggc ttcgccaacc ggaacttcat gcagctcatc    2280
```

```
cacgacgact ccctcacttt caaggaggac atccagaagg cccaggtcag cggacagggc    2340
gactcgctcc acgaacacat cgccaacctg gccgggtcgc ctgcgattaa aaagggaatc    2400
cttcagaccg tcaaggtcgt ggacgagctg gtgaaggtga tgggcaggca caagcccgaa    2460
aatatcgtca ttgagatggc ccgggagaac cagaccacgc agaaaggcca agaacagcc    2520 cgggagcgca tgaaacggat cgaggagggt atcaaggagc tgggctcgca gatcctcaag    2580
gagcaccctg tggaaaatac ccagctgcag aatgaaaagc tctacctcta ctacctccag    2640
aacggccgcg acatgtacgt ggaccaggag ctggacatta atcgcctctc ggactacgac    2700
gtcgaccaca tcgtcccgca gtccttcctg aaggacgaca gcatcgacaa caaggtcttg    2760
acccgctccg ataaaaatcg cgggaagtcc gacaacgtgc cgtcggagga ggtggtcaag    2820
aagatgaaaa actactggcg ccagctgctc aacgccaagc taatcacgca gcgcaagttc    2880
gacaacctca ccaaggccga acgcggcggt ctctccgagc ttgataaggc tgggttcatc    2940
aagagacagc tggtggagac ccggcagatc accaagcatg tcgcccagat cctggactcg    3000
cgcatgaata ctaagtacga tgaaaacgac aagctcatcc gcgaggtgaa ggtgatcacc    3060
ctgaagagca agctggtctc ggacttccgg aaggacttcc agttctacaa ggtccgggag    3120
atcaacaact accaccacgc gcacgacgcc tacctgaacg cggtggtggg cacagcccct    3180
ataaagaagt accctaagct cgagtccgag ttcgtgtacg gcgactacaa ggtgtacgac    3240
gtccgcaaga tgatcgcgaa gagcgagcag gagatcggga aggccaccgc aaaatacttc    3300
ttctactcca acatcatgaa cttcttcaag accgagatca ccctggccaa cggggagatc    3360
cgcaagcgcc cgctgattga cacgaacgga gagacaggcg agatagtctg ggacaagggc    3420
agggacttcg ccaccgtgcg caaggttctg tccatgccgc aggtgaacat cgtgaagaag    3480
actgaggtgc agacaggcgg cttctcgaag gagtccatcc tgcccaagcg aacagcgac     3540 aagctcatcg cgcggaagaa ggactgggac cctaaaaaat atggcgggtt cgactcgccc    3600
accgtggctt actcggtcct cgtggtggcc aaggtcgaga agggcaaaag caagaagctg    3660
aagagcgtca aggagctcct cggcatcacc atcatggagc ggtccagctt cgagaagaac    3720
ccgatcgact tcctcgaggc gaagggatat aaggaggtga agaaggacct catcattaaa    3780
ctgccgaagt actcgctatt cgaactggag aatggtcgca agaggatgct cgcgagcgct    3840
ggcgagctgc agaaagggaa cgagctggct ctcccgagca gtacgtcaa  cttcctctac    3900 ctggcctccc actatgaaaa gctcaagggc tcgccggagg acaacgagca gaagcagctg    3960
ttcgtcgagc agcacaagca ttacctcgac gagatcatcg agcagatctc ggagttcagc    4020
aagcgcgtga tcctggccga cgccaacctc gacaaggtgc tgtccgcata taacaagcac    4080
cgcgacaaac caatacggga gcaggccgaa aatatcatcc acctgttcac cctcacgaac    4140
ctgggcgccc ccgccgcgtt caagtacttc gacacaacca tcgaccgcaa gcggtacacg    4200
agcacgaagg aggtgctgga cgccacgttg attcaccagt ccatcacggg cctgtatgaa    4260
acaaggatcg atctcagcca gctcggcggc gactag                              4296
```

<210> SEQ ID NO 11
<211> LENGTH: 10
<212> TYPE: PRT
<213> ORGANISM: Simian virus

<400> SEQUENCE: 11

Met Ala Pro Lys Lys Lys Arg Lys Val His
1               5                   10

<210> SEQ ID NO 12
<211> LENGTH: 1000
<212> TYPE: DNA
<213> ORGANISM: Zea mays

<400> SEQUENCE: 12

| | |
|---|---|
| tgagagtaca atgatgaacc tagattaatc aatgccaaag tctgaaaaat gcaccctcag | 60 |
| tctatgatcc agaaaatcaa gattgcttga ggccctgttc ggttgttccg gattagagcc | 120 |
| ccggattaat tcctagccgg attacttctc taatttatat agattttgat gagctggaat | 180 |
| gaatcctggc ttattccggt acaaccgaac aggccctgaa ggataccagt aatcgctgag | 240 |
| ctaaattggc atgctgtcag agtgtcagta ttgcagcaag gtagtgagat aaccggcatc | 300 |
| atggtgccag tttgatggca ccattagggt tagagatggt ggccatgggc gcatgtcctg | 360 |
| gccaactttg tatgatatat ggcagggtga ataggaaagt aaaattgtat tgtaaaaagg | 420 |
| gatttcttct gtttgttagc gcatgtacaa ggaatgcaag ttttgagcga gggggcatca | 480 |
| aagatctggc tgtgtttcca gctgttttg ttagccccat cgaatccttg acataatgat | 540 |
| cccgcttaaa taagcaacct cgcttgtata gttccttgtg ctctaacaca cgatgatgat | 600 |
| aagtcgtaaa atagtggtgt ccaaagaatt tccaggccca gttgtaaaag ctaaaatgct | 660 |
| attcgaattt ctactagcag taagtcgtgt ttagaaatta ttttttttata tacctttttt | 720 |
| ccttctatgt acagtaggac acagtgtcag cgccgcgttg acggagaata tttgcaaaaa | 780 |
| agtaaaagag aaagtcatag cggcgtatgt gccaaaaact tcgtcacaga gagggccata | 840 |
| agaaacatgg cccacggccc aatacgaagc accgcgacga agcccaaaca gcagtccgta | 900 |
| ggtggagcaa agcgctgggt aatacgcaaa cgttttgtcc caccttgact aatcacaaga | 960 |
| gtggagcgta ccttataaac cgagccgcaa gcaccgaatt | 1000 |

<210> SEQ ID NO 13
<211> LENGTH: 1105
<212> TYPE: DNA
<213> ORGANISM: Artificial
<220> FEATURE:
<223> OTHER INFORMATION: WXY-CR4 gRNA expression cassette

<400> SEQUENCE: 13

| | |
|---|---|
| tgagagtaca atgatgaacc tagattaatc aatgccaaag tctgaaaaat gcaccctcag | 60 |
| tctatgatcc agaaaatcaa gattgcttga ggccctgttc ggttgttccg gattagagcc | 120 |
| ccggattaat tcctagccgg attacttctc taatttatat agattttgat gagctggaat | 180 |
| gaatcctggc ttattccggt acaaccgaac aggccctgaa ggataccagt aatcgctgag | 240 |
| ctaaattggc atgctgtcag agtgtcagta ttgcagcaag gtagtgagat aaccggcatc | 300 |
| atggtgccag tttgatggca ccattagggt tagagatggt ggccatgggc gcatgtcctg | 360 |
| gccaactttg tatgatatat ggcagggtga ataggaaagt aaaattgtat tgtaaaaagg | 420 |
| gatttcttct gtttgttagc gcatgtacaa ggaatgcaag ttttgagcga gggggcatca | 480 |
| aagatctggc tgtgtttcca gctgttttg ttagccccat cgaatccttg acataatgat | 540 |
| cccgcttaaa taagcaacct cgcttgtata gttccttgtg ctctaacaca cgatgatgat | 600 |
| aagtcgtaaa atagtggtgt ccaaagaatt tccaggccca gttgtaaaag ctaaaatgct | 660 |
| attcgaattt ctactagcag taagtcgtgt ttagaaatta ttttttttata tacctttttt | 720 |
| ccttctatgt acagtaggac acagtgtcag cgccgcgttg acggagaata tttgcaaaaa | 780 |

```
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gcccaaaacg ctttcccgat   1020
gttttagagc tagaaatagc aagttaaaat aaggctagtc cgttatcaac ttgaaaaagt   1080
ggcaccgagt cggtgctttt ttttt                                         1105
```

<210> SEQ ID NO 14
<211> LENGTH: 1104
<212> TYPE: DNA
<213> ORGANISM: Artificial
<220> FEATURE:
<223> OTHER INFORMATION: WXY-CR8 gRNA expression cassette

<400> SEQUENCE: 14

```
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga gggggcatca    480
aagatctggc tgtgtttcca gctgtttttg ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaaatgct    660
attcgaattt ctactagcag taagtcgtgt ttagaaatta tttttttata taccttttt    720 ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gcaatataaa attaccgatg   1020
ttttagagct agaaatagca agttaaaata aggctagtcc gttatcaact tgaaaaagtg   1080
gcaccgagtc ggtgcttttt tttt                                          1104
```

<210> SEQ ID NO 15
<211> LENGTH: 1106
<212> TYPE: DNA
<213> ORGANISM: Artificial
<220> FEATURE:
<223> OTHER INFORMATION: WXY-CR10 gRNA expression cassette

<400> SEQUENCE: 15

```
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
```

```
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga ggggggcatca   480 aagatctggc tgtgttttcca gctgttttttg ttagccccat cgaatccttg acataatgat  540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata taccttttttt  720 ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta cctataaaac cgagccgcaa gcaccgaatt gctgggagag acggtgtagt  1020
agttttagag ctagaaatag caagttaaaa taaggctagt ccgttatcaa cttgaaaaag  1080
tggcaccgag tcggtgcttt tttttt                                        1106
```

<210> SEQ ID NO 16
<211> LENGTH: 1104
<212> TYPE: DNA
<213> ORGANISM: Artificial
<220> FEATURE:
<223> OTHER INFORMATION: WXY-CR1 gRNA expression cassette

<400> SEQUENCE: 16

```
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga ggggggcatca  480 aagatctggc tgtgttttcca gctgttttttg ttagccccat cgaatccttg acataatgat 540
cccgcttaaa taagcaacct cgcttgtata gttccttgtg ctctaacaca cgatgatgat  600
aagtcgtaaa atagtggtgt ccaaagaatt tccaggccca gttgtaaaag ctaaaatgct  660
attcgaattt ctactagcag taagtcgtgt ttagaaatta ttttttttata taccttttttt 720 ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta cctataaaac cgagccgcaa gcaccgaatt ggcatctaca gggacgcaag 1020
ttttagagct agaaatagca agttaaaata aggctagtcc gttatcaact tgaaaagtg  1080 gcaccgagtc ggtgcttttt tttt                                         1104
```

<210> SEQ ID NO 17

<211> LENGTH: 1103
<212> TYPE: DNA
<213> ORGANISM: Artificial
<220> FEATURE:
<223> OTHER INFORMATION: WXY-CR3 gRNA expression cassette

<400> SEQUENCE: 17

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgtttcca gctgttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta tttttttata tacctttttt     720
ccttctatgt acagtaggac acagtgtcag cgccgcgttg acggagaata tttgcaaaaa     780
agtaaaagag aaagtcatag cggcgtatgt gccaaaaact tcgtcacaga gagggccata     840
agaaacatgg cccacggccc aatacgaagc accgcgacga agcccaaaca gcagtccgta     900
ggtggagcaa agcgctgggt aatacgcaaa cgttttgtcc caccttgact aatcacaaga     960
gtggagcgta ccttataaac cgagccgcaa gcaccgaatt gagcatggag aacgaaaagt    1020
tttagagcta gaaatagcaa gttaaaataa ggctagtccg ttatcaactt gaaaaagtgg    1080
caccgagtcg gtgcttttt ttt                                            1103
```

<210> SEQ ID NO 18
<211> LENGTH: 1103
<212> TYPE: DNA
<213> ORGANISM: Artificial
<220> FEATURE:
<223> OTHER INFORMATION: WXY-CR2 gRNA expression cassette

<400> SEQUENCE: 18

```
tgagagtaca atgatgaacc tagattaatc aatgccaaag tctgaaaaat gcaccctcag      60
tctatgatcc agaaaatcaa gattgcttga ggccctgttc ggttgttccg gattagagcc     120
ccggattaat tcctagccgg attacttctc taatttatat agattttgat gagctggaat     180
gaatcctggc ttattccggt acaaccgaac aggccctgaa ggataccagt aatcgctgag     240
ctaaattggc atgctgtcag agtgtcagta ttgcagcaag gtagtgagat aaccggcatc     300
atggtgccag tttgatggca ccattagggt tagagatggt ggccatgggc gcatgtcctg     360
gccaactttg tatgatatat ggcagggtga ataggaaagt aaaattgtat tgtaaaaagg     420
gatttcttct gtttgttagc gcatgtacaa ggaatgcaag ttttgagcga gggggcatca     480
aagatctggc tgtgtttcca gctgttttg ttagccccat cgaatccttg acataatgat     540
cccgcttaaa taagcaacct cgcttgtata gttccttgtg ctctaacaca cgatgatgat     600
aagtcgtaaa atagtggtgt ccaaagaatt tccaggccca gttgtaaaag ctaaaatgct     660
attcgaattt ctactagcag taagtcgtgt ttagaaatta tttttttata tacctttttt     720
```

```
ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gctcgtatat acctcgtcgt   1020
tttagagcta gaaatagcaa gttaaaataa ggctagtccg ttatcaactt gaaaaagtgg   1080
caccgagtcg gtgcttttt ttt                                            1103
```

<210> SEQ ID NO 19
<211> LENGTH: 1104
<212> TYPE: DNA
<213> ORGANISM: Artificial
<220> FEATURE:
<223> OTHER INFORMATION: WXY-CR6 gRNA expression cassette

<400> SEQUENCE: 19

```
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga gggggcatca    480
aagatctggc tgtgtttcca gctgtttttg ttagccccat cgaatccttg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaaatgct    660
attcgaattt ctactagcag taagtcgtgt ttagaaatta ttttttttata tacctttttt    720 ccttctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gctggtgcgc agtgccgggg   1020
ttttagagct agaaatagca agttaaaata aggctagtcc gttatcaact tgaaaaagtg   1080
gcaccgagtc ggtgcttttt tttt                                          1104
```

<210> SEQ ID NO 20
<211> LENGTH: 1103
<212> TYPE: DNA
<213> ORGANISM: Artificial
<220> FEATURE:
<223> OTHER INFORMATION: WXY-CR7 gRNA expression cassette

<400> SEQUENCE: 20

```
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
```

```
gaatcctggc ttattccggt acaaccgaac aggccctgaa ggataccagt aatcgctgag      240
ctaaattggc atgctgtcag agtgtcagta ttgcagcaag gtagtgagat aaccggcatc      300
atggtgccag tttgatggca ccattagggt tagagatggt ggccatgggc gcatgtcctg      360
gccaactttg tatgatatat ggcagggtga ataggaaagt aaaattgtat tgtaaaaagg      420
gatttcttct gtttgttagc gcatgtacaa ggaatgcaag ttttgagcga gggggcatca      480
aagatctggc tgtgtttcca gctgtttttg ttagccccat cgaatccttg acataatgat      540
cccgcttaaa taagcaacct cgcttgtata gttccttgtg ctctaacaca cgatgatgat      600
aagtcgtaaa atagtggtgt ccaaagaatt ccaggccca gttgtaaaag ctaaaatgct       660
attcgaattt ctactagcag taagtcgtgt ttagaaatta ttttttttata taccttttttt    720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt gagaccatag cctatcttgt     1020
tttagagcta gaaatagcaa gttaaaataa ggctagtccg ttatcaactt gaaaaagtgg     1080
caccgagtcg gtgcttttttt tttt                                           1103
```

<210> SEQ ID NO 21
<211> LENGTH: 1106
<212> TYPE: DNA
<213> ORGANISM: Artificial
<220> FEATURE:
<223> OTHER INFORMATION: WXY-CR5 gRNA expression cassette

<400> SEQUENCE: 21

```
tgagagtaca atgatgaacc tagattaatc aatgccaaag tctgaaaaat gcaccctcag       60
tctatgatcc agaaaatcaa gattgcttga ggccctgttc ggttgttccg gattagagcc      120
ccggattaat tcctagccgg attacttctc taatttatat agattttgat gagctggaat      180
gaatcctggc ttattccggt acaaccgaac aggccctgaa ggataccagt aatcgctgag      240
ctaaattggc atgctgtcag agtgtcagta ttgcagcaag gtagtgagat aaccggcatc      300
atggtgccag tttgatggca ccattagggt tagagatggt ggccatgggc gcatgtcctg      360
gccaactttg tatgatatat ggcagggtga ataggaaagt aaaattgtat tgtaaaaagg      420
gatttcttct gtttgttagc gcatgtacaa ggaatgcaag ttttgagcga gggggcatca      480
aagatctggc tgtgtttcca gctgtttttg ttagccccat cgaatccttg acataatgat      540
cccgcttaaa taagcaacct cgcttgtata gttccttgtg ctctaacaca cgatgatgat      600
aagtcgtaaa atagtggtgt ccaaagaatt ccaggccca gttgtaaaag ctaaaatgct       660
attcgaattt ctactagcag taagtcgtgt ttagaaatta ttttttttata taccttttttt    720 ccttctatgt acagtaggac acagtgtcag cgccgcgttg acggagaata tttgcaaaaa      780
agtaaaagag aaagtcatag cggcgtatgt gccaaaaact tcgtcacaga gagggccata      840
agaaacatgg cccacggccc aatacgaagc accgcgacga agcccaaaca gcagtccgta      900
ggtggagcaa agcgctgggt aatacgcaaa cgttttgtcc caccttgact aatcacaaga      960
gtggagcgta ccttataaac cgagccgcaa gcaccgaatt gacaatgccc taaatatcta     1020
tgttttagag ctagaaatag caagttaaaa taaggctagt ccgttatcaa cttgaaaaag     1080
tggcaccgag tcggtgcttt tttttt                                          1106
```

<210> SEQ ID NO 22
<211> LENGTH: 97
<212> TYPE: DNA
<213> ORGANISM: Artificial
<220> FEATURE:
<223> OTHER INFORMATION: WXY-CR4 DNA version of gRNA

<400> SEQUENCE: 22
gcccaaaacg ctttcccgat gttttagagc tagaaatagc aagttaaaat aaggctagtc    60
cgttatcaac ttgaaaaagt ggcaccgagt cggtgct                             97

<210> SEQ ID NO 23
<211> LENGTH: 96
<212> TYPE: DNA
<213> ORGANISM: Artificial
<220> FEATURE:
<223> OTHER INFORMATION: WXY-CR8 DNA version of gRNA

<400> SEQUENCE: 23
gcaatataaa attaccgatg ttttagagct agaaatagca agttaaaata aggctagtcc    60
gttatcaact tgaaaaagtg gcaccgagtc ggtgct                              96

<210> SEQ ID NO 24
<211> LENGTH: 98
<212> TYPE: DNA
<213> ORGANISM: Artificial
<220> FEATURE:
<223> OTHER INFORMATION: WXY-CR10 DNA version of gRNA

<400> SEQUENCE: 24
gctgggagag acggtgtagt agttttagag ctagaaatag caagttaaaa taaggctagt    60
ccgttatcaa cttgaaaaag tggcaccgag tcggtgct                            98

<210> SEQ ID NO 25
<211> LENGTH: 96
<212> TYPE: DNA
<213> ORGANISM: Artificial
<220> FEATURE:
<223> OTHER INFORMATION: WXY-CR1 DNA version of gRNA

<400> SEQUENCE: 25
ggcatctaca gggacgcaag ttttagagct agaaatagca agttaaaata aggctagtcc    60
gttatcaact tgaaaaagtg gcaccgagtc ggtgct                              96

<210> SEQ ID NO 26
<211> LENGTH: 95
<212> TYPE: DNA
<213> ORGANISM: Artificial
<220> FEATURE:
<223> OTHER INFORMATION: WXY-CR3 DNA version of gRNA

<400> SEQUENCE: 26
gagcatggag aacgaaaagt tttagagcta gaaatagcaa gttaaaataa ggctagtccg    60
ttatcaactt gaaaagtgg caccgagtcg gtgct                                95

<210> SEQ ID NO 27
<211> LENGTH: 95
<212> TYPE: DNA
<213> ORGANISM: Artificial
<220> FEATURE:
<223> OTHER INFORMATION: WXY-CR2 DNA version of gRNA

<400> SEQUENCE: 27
gctcgtatat acctcgtcgt tttagagcta gaaatagcaa gttaaaataa ggctagtccg    60
ttatcaactt gaaaaagtgg caccgagtcg gtgct                              95

<210> SEQ ID NO 28
<211> LENGTH: 96
<212> TYPE: DNA
<213> ORGANISM: Artificial
<220> FEATURE:
<223> OTHER INFORMATION: WXY-CR6 DNA version of gRNA

<400> SEQUENCE: 28
gctggtgcgc agtgccgggg ttttagagct agaaatagca agttaaaata aggctagtcc    60
gttatcaact tgaaaaagtg gcaccgagtc ggtgct                             96

<210> SEQ ID NO 29
<211> LENGTH: 95
<212> TYPE: DNA
<213> ORGANISM: Artificial
<220> FEATURE:
<223> OTHER INFORMATION: WXY-CR7 DNA version of gRNA

<400> SEQUENCE: 29
gagaccatag cctatcttgt tttagagcta gaaatagcaa gttaaaataa ggctagtccg    60
ttatcaactt gaaaaagtgg caccgagtcg gtgct                              95

<210> SEQ ID NO 30
<211> LENGTH: 98
<212> TYPE: DNA
<213> ORGANISM: Artificial
<220> FEATURE:
<223> OTHER INFORMATION: WXY-CR5 DNA version of gRNA

<400> SEQUENCE: 30
gacaatgccc taaatatcta tgttttagag ctagaaatag caagttaaaa taaggctagt    60
ccgttatcaa cttgaaaaag tggcaccgag tcggtgct                           98

<210> SEQ ID NO 31
<211> LENGTH: 18
<212> TYPE: DNA
<213> ORGANISM: Artificial
<220> FEATURE:
<223> OTHER INFORMATION: P4F forward primer

<400> SEQUENCE: 31
gtgtgcgtgc gtgcagac                                                 18

<210> SEQ ID NO 32
<211> LENGTH: 24
<212> TYPE: DNA
<213> ORGANISM: Artificial
<220> FEATURE:
<223> OTHER INFORMATION: P8R reverse primer

<400> SEQUENCE: 32
agcagggatt atttactcca ccac                                          24

<210> SEQ ID NO 33
<211> LENGTH: 19
<212> TYPE: DNA
<213> ORGANISM: Artificial
<220> FEATURE:
<223> OTHER INFORMATION: P7R Reverse primer

```
<400> SEQUENCE: 33
gccagaagct gccagaagc                                                    19

<210> SEQ ID NO 34
<211> LENGTH: 27
<212> TYPE: DNA
<213> ORGANISM: Artificial
<220> FEATURE:
<223> OTHER INFORMATION: P5R Reverse primer

<400> SEQUENCE: 34
gctaaatgta ggtgaatgaa acaagaa                                           27

<210> SEQ ID NO 35
<211> LENGTH: 15
<212> TYPE: DNA
<213> ORGANISM: Artificial
<220> FEATURE:
<223> OTHER INFORMATION: CR4 probe

<400> SEQUENCE: 35
caagccaagg cgagg                                                        15

<210> SEQ ID NO 36
<211> LENGTH: 26
<212> TYPE: DNA
<213> ORGANISM: Artificial
<220> FEATURE:
<223> OTHER INFORMATION: P10F Forward primer

<400> SEQUENCE: 36
catatggaga ggttaagaca gcaatt                                            26

<210> SEQ ID NO 37
<211> LENGTH: 18
<212> TYPE: DNA
<213> ORGANISM: Artificial
<220> FEATURE:
<223> OTHER INFORMATION: CR10 probe

<400> SEQUENCE: 37
aatttgatgc cgtcctat                                                     18

<210> SEQ ID NO 38
<211> LENGTH: 58
<212> TYPE: DNA
<213> ORGANISM: Artificial
<220> FEATURE:
<223> OTHER INFORMATION: NGS 2nd Forward primer

<400> SEQUENCE: 38
aatgatacgg cgaccaccga gatctacaca tacgagatcc gtaatcggga agctgaag         58

<210> SEQ ID NO 39
<211> LENGTH: 56
<212> TYPE: DNA
<213> ORGANISM: Artificial
<220> FEATURE:
<223> OTHER INFORMATION: NGS 2nd reverse primer
<220> FEATURE:
<221> NAME/KEY: misc_feature
<222> LOCATION: (25)..(32)
<223> OTHER INFORMATION: n is a, c, g, or t

<400> SEQUENCE: 39
```
caagcagaag acggcatacg agatnnnnnn nnacacgcac gatccgacgg tagtgt        56

<210> SEQ ID NO 40
<211> LENGTH: 35
<212> TYPE: DNA
<213> ORGANISM: Artificial
<220> FEATURE:
<223> OTHER INFORMATION: NGS 1st CR4/CR6 mipf1 Forward primer

<400> SEQUENCE: 40
atcgggaagc tgaagtgcgt gcgtgcagac gacaa                               35

<210> SEQ ID NO 41
<211> LENGTH: 39
<212> TYPE: DNA
<213> ORGANISM: Artificial
<220> FEATURE:
<223> OTHER INFORMATION: NGS 1st CR8mipr Reverse primer

<400> SEQUENCE: 41
atccgacggt agtgtgagga gcgataagaa caccgaaca                           39

<210> SEQ ID NO 42
<211> LENGTH: 41
<212> TYPE: DNA
<213> ORGANISM: Artificial
<220> FEATURE:
<223> OTHER INFORMATION: NGS 1st CR5mipr Reverse primer

<400> SEQUENCE: 42
atccgacggt agtgtaaatg taggtgaats aaacaagaaa c                        41

<210> SEQ ID NO 43
<211> LENGTH: 48
<212> TYPE: DNA
<213> ORGANISM: Artificial
<220> FEATURE:
<223> OTHER INFORMATION: NGS 1st CR7mipr Reverse primer

<400> SEQUENCE: 43
atccgacggt agtgtggatc tagaaagtga cagattccta atattaca                 48

<210> SEQ ID NO 44
<211> LENGTH: 42
<212> TYPE: DNA
<213> ORGANISM: Artificial
<220> FEATURE:
<223> OTHER INFORMATION: NGS 1st CR10mipf Forward primer

<400> SEQUENCE: 44
atcgggaagc tgaagggtta agacagcaat taatttgatg cc                       42

<210> SEQ ID NO 45
<211> LENGTH: 36
<212> TYPE: DNA
<213> ORGANISM: Artificial
<220> FEATURE:
<223> OTHER INFORMATION: NGS 1st CR1mipf Forward primer

<400> SEQUENCE: 45
atcgggaagc tgaaggccct ctctcgtgct acctca                              36

<210> SEQ ID NO 46
<211> LENGTH: 40
<212> TYPE: DNA
<213> ORGANISM: Artificial

<220> FEATURE:
<223> OTHER INFORMATION: NGS 1st CR1mipr Reverse primer

<400> SEQUENCE: 46
atccgacggt agtgtgaaga tggtcagaca gacatgcagt                40

<210> SEQ ID NO 47
<211> LENGTH: 57
<212> TYPE: DNA
<213> ORGANISM: Zea mays

<400> SEQUENCE: 47
aggcagcccc cgatcggtaa ttttatattg cgagtaaata aatggacctg tagtggt    57

<210> SEQ ID NO 48
<211> LENGTH: 57
<212> TYPE: DNA
<213> ORGANISM: Artificial
<220> FEATURE:
<223> OTHER INFORMATION: Deletion mutant at CR4/CR8 junction

<400> SEQUENCE: 48
aggcagcccc cgatcggtaa ttttatattg cgagtaaata aatggacctg tagtggt    57

<210> SEQ ID NO 49
<211> LENGTH: 56
<212> TYPE: DNA
<213> ORGANISM: Artificial
<220> FEATURE:
<223> OTHER INFORMATION: Deletion mutant at CR4/CR8 junction

<400> SEQUENCE: 49
aggcagcccc cgatcgtaat tttatattgc gagtaaataa atggacctgt agtggt    56

<210> SEQ ID NO 50
<211> LENGTH: 55
<212> TYPE: DNA
<213> ORGANISM: Artificial
<220> FEATURE:
<223> OTHER INFORMATION: Deletion mutant at CR4/CR8 junction

<400> SEQUENCE: 50
aggcagcccc cgatctaatt ttatattgcg agtaaataaa tggacctgta gtggt    55

<210> SEQ ID NO 51
<211> LENGTH: 51
<212> TYPE: DNA
<213> ORGANISM: Artificial
<220> FEATURE:
<223> OTHER INFORMATION: Deletion mutant at CR4/CR8 junction

<400> SEQUENCE: 51
aggcagcccc cgatctttat attgcgagta aataaatgga cctgtagtgg t    51

<210> SEQ ID NO 52
<211> LENGTH: 50
<212> TYPE: DNA
<213> ORGANISM: Artificial
<220> FEATURE:
<223> OTHER INFORMATION: Deletion mutant at CR4/CR8 junction

<400> SEQUENCE: 52
aggcagcccc cgattttata ttgcgagtaa ataaatggac ctgtagtggt    50

<210> SEQ ID NO 53

-continued

```
<211> LENGTH: 49
<212> TYPE: DNA
<213> ORGANISM: Artificial
<220> FEATURE:
<223> OTHER INFORMATION: Deletion mutant at CR4/CR8 junction

<400> SEQUENCE: 53
aggcagcccc cgatttatat tgcgagtaaa taaatggacc tgtagtggt                49

<210> SEQ ID NO 54
<211> LENGTH: 56
<212> TYPE: DNA
<213> ORGANISM: Artificial
<220> FEATURE:
<223> OTHER INFORMATION: Deletion mutant at CR4/CR8 junction

<400> SEQUENCE: 54
aggcagcccc cgatggtaat tttatattgc gagtaaataa atggacctgt agtggt        56

<210> SEQ ID NO 55
<211> LENGTH: 52
<212> TYPE: DNA
<213> ORGANISM: Artificial
<220> FEATURE:
<223> OTHER INFORMATION: Deletion mutant at CR4/CR8 junction

<400> SEQUENCE: 55
aggcagcccc cgtaatttta tattgcgagt aaataaatgg acctgtagtg gt            52

<210> SEQ ID NO 56
<211> LENGTH: 50
<212> TYPE: DNA
<213> ORGANISM: Artificial
<220> FEATURE:
<223> OTHER INFORMATION: Deletion mutant at CR4/CR8 junction

<400> SEQUENCE: 56
aggcagcccc cgatcttata ttgcgagtaa ataaatggac ctgtagtggt               50

<210> SEQ ID NO 57
<211> LENGTH: 49
<212> TYPE: DNA
<213> ORGANISM: Artificial
<220> FEATURE:
<223> OTHER INFORMATION: Deletion mutant at CR4/CR8 junction

<400> SEQUENCE: 57
aggcagcccc cgatctatat tgcgagtaaa taaatggacc tgtagtggt                49

<210> SEQ ID NO 58
<211> LENGTH: 60
<212> TYPE: DNA
<213> ORGANISM: Zea mays

<400> SEQUENCE: 58
acatgtcaaa gtgctgggag agacggtgta ggtaatttta tattgcgagt aaataaatgg    60

<210> SEQ ID NO 59
<211> LENGTH: 60
<212> TYPE: DNA
<213> ORGANISM: Artificial
<220> FEATURE:
<223> OTHER INFORMATION: Deletion mutant at CR10/CR8 junction

<400> SEQUENCE: 59
acatgtcaaa gtgctgggag agacggtgta ggtaatttta tattgcgagt aaataaatgg    60
```

```
<210> SEQ ID NO 60
<211> LENGTH: 59
<212> TYPE: DNA
<213> ORGANISM: Artificial
<220> FEATURE:
<223> OTHER INFORMATION: Deletion mutant at CR10/CR8 junction

<400> SEQUENCE: 60
acatgtcaaa gtgctgggag agacggtgtg gtaattttat attgcgagta aataaatgg      59

<210> SEQ ID NO 61
<211> LENGTH: 58
<212> TYPE: DNA
<213> ORGANISM: Artificial
<220> FEATURE:
<223> OTHER INFORMATION: Deletion mutant at CR10/CR8 junction

<400> SEQUENCE: 61
acatgtcaaa gtgctgggag agacggtgta taattttata ttgcgagtaa ataaatgg       58

<210> SEQ ID NO 62
<211> LENGTH: 56
<212> TYPE: DNA
<213> ORGANISM: Artificial
<220> FEATURE:
<223> OTHER INFORMATION: Deletion mutant at CR10/CR8 junction

<400> SEQUENCE: 62
acatgtcaaa gtgctgggag agacggggta attttatatt gcgagtaaat aaatgg         56

<210> SEQ ID NO 63
<211> LENGTH: 54
<212> TYPE: DNA
<213> ORGANISM: Artificial
<220> FEATURE:
<223> OTHER INFORMATION: Deletion mutant at CR10/CR8 junction

<400> SEQUENCE: 63
acatgtcaaa gtgctgggag agacggtgat tttatattgc gagtaaataa atgg           54

<210> SEQ ID NO 64
<211> LENGTH: 57
<212> TYPE: DNA
<213> ORGANISM: Artificial
<220> FEATURE:
<223> OTHER INFORMATION: Deletion mutant at CR10/CR8 junction

<400> SEQUENCE: 64
acatgtcaaa gtgctgggag agacggtgtt aatttatat tgcgagtaaa taaatgg         57

<210> SEQ ID NO 65
<211> LENGTH: 53
<212> TYPE: DNA
<213> ORGANISM: Artificial
<220> FEATURE:
<223> OTHER INFORMATION: Deletion mutant at CR10/CR8 junction

<400> SEQUENCE: 65
acatgtcaaa gtgctgggag agacgtaatt ttatattgcg agtaaataaa tgg            53

<210> SEQ ID NO 66
<211> LENGTH: 33
<212> TYPE: DNA
<213> ORGANISM: Artificial
<220> FEATURE:
```

<223> OTHER INFORMATION: Deletion mutant at CR10/CR8 junction

<400> SEQUENCE: 66
acatgtaatt ttatattgcg agtaaataaa tgg                                     33

<210> SEQ ID NO 67
<211> LENGTH: 64
<212> TYPE: DNA
<213> ORGANISM: Artificial
<220> FEATURE:
<223> OTHER INFORMATION: Deletion mutant at CR10/CR8 junction

<400> SEQUENCE: 67
acatgtcaaa gtgctgggag agacggtgta acatgtcaaa gtgctgggag agacggtgta        60
gggg                                                                    64

<210> SEQ ID NO 68
<211> LENGTH: 72
<212> TYPE: DNA
<213> ORGANISM: Zea mays

<400> SEQUENCE: 68
tcccacggca tctacaggga cgcaaaggtt gccttctctg aactgaacaa cgccgtcttc        60
gttctccatg ct                                                           72

<210> SEQ ID NO 69
<211> LENGTH: 42
<212> TYPE: DNA
<213> ORGANISM: Artificial
<220> FEATURE:
<223> OTHER INFORMATION: Deletion mutants at CR1 or CR1/CR3 junction

<400> SEQUENCE: 69
tcccacggca tctacaggga cgccgtcttc gttctccatg ct                          42

<210> SEQ ID NO 70
<211> LENGTH: 71
<212> TYPE: DNA
<213> ORGANISM: Artificial
<220> FEATURE:
<223> OTHER INFORMATION: Deletion mutants at CR1 or CR1/CR3 junction

<400> SEQUENCE: 70
tcccacggca tctacaggga ccaaaggttg ccttctctga actgaacaac gccgtcttcg        60
ttctccatgc t                                                            71

<210> SEQ ID NO 71
<211> LENGTH: 71
<212> TYPE: DNA
<213> ORGANISM: Artificial
<220> FEATURE:
<223> OTHER INFORMATION: Deletion mutants at CR1 or CR1/CR3 junction

<400> SEQUENCE: 71
tcccacggca tctacaggga cgaaaggttg ccttctctga actgaacaac gccgtcttcg        60
ttctccatgc t                                                            71

<210> SEQ ID NO 72
<211> LENGTH: 70
<212> TYPE: DNA
<213> ORGANISM: Artificial
<220> FEATURE:
<223> OTHER INFORMATION: Deletion mutants at CR1 or CR1/CR3 junction

```
<400> SEQUENCE: 72
tcccacggca tctacaggga caaaggttgc cttctctgaa ctgaacaacg ccgtcttcgt    60
tctccatgct                                                          70

<210> SEQ ID NO 73
<211> LENGTH: 64
<212> TYPE: DNA
<213> ORGANISM: Artificial
<220> FEATURE:
<223> OTHER INFORMATION: Deletion mutants at CR1 or CR1/CR3 junction

<400> SEQUENCE: 73
tcccacggca tctgcaaagg ttgccttctc tgaactgaac aacgccgtct tcgttctcca    60
tgct                                                                64

<210> SEQ ID NO 74
<211> LENGTH: 62
<212> TYPE: DNA
<213> ORGANISM: Artificial
<220> FEATURE:
<223> OTHER INFORMATION: Deletion mutants at CR1 or CR1/CR3 junction

<400> SEQUENCE: 74
tcccacggca tgcaaaggtt gccttctctg aactgaacaa cgccgtcttc gttctccatg    60
ct                                                                  62

<210> SEQ ID NO 75
<211> LENGTH: 36
<212> TYPE: DNA
<213> ORGANISM: Artificial
<220> FEATURE:
<223> OTHER INFORMATION: Deletion mutants at CR1 or CR1/CR3 junction

<400> SEQUENCE: 75
tcccacggca tctacaggga cgtcgttctc catgct                             36

<210> SEQ ID NO 76
<211> LENGTH: 60
<212> TYPE: DNA
<213> ORGANISM: Artificial
<220> FEATURE:
<223> OTHER INFORMATION: Deletion mutants at CR1 or CR1/CR3 junction

<400> SEQUENCE: 76
tcccacggca tctacagtgc cttctctgaa ctgaacaacg ccgtcttcgt tctccatgct   60
```

WAXY CORN

CROSS REFERENCE TO RELATED APPLICATIONS

This application claims the benefit of International Application Number PCT/US2017/014903 filed Jan. 25, 2017, which claims the benefit of U.S. Provisional Application No. 62/287,115, filed Jan. 26, 2016, the entire content of which is herein incorporated by reference.

FIELD

The field is molecular biology, and more specifically, methods for editing the genome of a maize plant cell to produce Waxy corn.

REFERENCE TO SEQUENCE LISTING SUBMITTED ELECTRONICALLY

The official copy of the sequence listing is submitted electronically via EFS-Web as an ASCII formatted sequence listing with a file named 20170116_BB2535PCT_SequenceListing_ST25.txt created on Jan. 16, 2017 and having a size of 35 kilobytes and is filed concurrently with the specification. The sequence listing contained in this ASCII formatted document is part of the specification and is herein incorporated by reference in its entirety.

BACKGROUND

Maize kernels consist primarily of starch which is composed of two types of polysaccharides—amylose and amylopectin. In normal dent maize, the ratio between amylose and amylopectin is approximately 27% to 73%. In "Waxy" corn, however, the starch is composed exclusively of amylopectin and is a valuable commodity due to its superior properties, including but not limited to a higher hot viscosity; production of softer, more stable, and clearer gels; and higher freeze-thaw stability. The starch from Waxy maize has appreciable end uses in industrial and food-grade product streams, such as, for example, as ingredients (thickeners), adhesives and bioplastics, ethanol fermentation, and possibly in silage.

The Waxy (Wx1) gene in maize encodes a granule-bound starch synthase enzyme, NDP-glucose-starch glucosyltransferase, that is responsible for production of amylose in pollen and endosperm tissue. When the Waxy gene is knocked out, as in recessive (wx1) alleles, "Waxy" maize, or maize with high amylopectin starch in its pollen and kernels, results. There are more than 40 mutant alleles known for the Waxy locus, and producing Waxy maize typically involves breeding a mutant allele into modern maize inbreds for the production of industrial hybrids. However, the mutant alleles are recessive, which can make the breeding process cumbersome, requiring substantial time and resources. Moreover, the resulting products may have quality issues; and the trait may exhibit incomplete penetrance. Most importantly, there is often a yield penalty associated with introgression of the waxy trait.

There is a need to produce Waxy maize more efficiently and in a way that will reduce yield drag associated with introgression of Waxy mutant alleles into elite maize lines via conventional means.

SUMMARY

The methods described herein relate to the generation of maize lines with mutations that knock out the Waxy (Wx1) gene. Compositions and methods are provided for editing of the Wx1 gene locus in a maize plant cell.

Methods for obtaining a Waxy maize plant are presented herein in which double strand breaks are introduced into one or more target sites in an endogenous WX1 encoding sequence in a maize plant cell to produce a maize plant cell with a modified Wx1 nucleotide sequence, wherein the modified Wx1 nucleotide sequence comprises a nucleic acid alteration that knocks out Wx1 gene function. A maize plant is generated from the maize plant cell; and the maize plant produces grain with an increased percentage of amylopectin compared to a second maize plant comprising a functional Wx1 gene. The method may further include introducing a Wx1 polynucleotide modification template in the maize plant cell, in which the Wx1 polynucleotide modification template has at least one nucleic acid alteration (when compared to the endogenous WX1 encoding sequence) that knocks out Wx1 gene function when incorporated into the endogenous WX1 encoding sequence. The double strand break may be induced by a TALEN, a meganuclease, a zinc finger nuclease, a CRISPR-associated nuclease, or any other double strand inducing agent known to one of ordinary skill in the art.

In some aspects, the double strand inducing agent is a CRISPR-associated nuclease and one or more guide RNAs are provided. In these methods, one or more guide RNAs and a Cas endonuclease are provided to a maize plant cell comprising an endogenous WX1 encoding sequence, in which each guide RNA is capable of forming a complex with Cas endonuclease that enables the Cas endonuclease to introduce a double strand break at a target site in the endogenous WX1 encoding sequence in the genome of the maize plant cell. Alternatively, one or more guide RNAs are provided to a maize plant cell comprising a Cas endonuclease and a an endogenous WX1 encoding sequence, wherein each guide RNA is capable of forming a complex with Cas endonuclease that enables the Cas endonuclease to introduce a double strand break at a target site in the endogenous WX1 encoding sequence in the genome of said maize plant cell. In either method, maize plants are obtained from the maize plant cells; and the maize plants may or may not be evaluated for the presence of a nucleic acid alteration that knocks out the function of the Wx1 gene. A maize plant that produces grain with an increased percentage of amylopectin compared to a second maize plant comprising a functional Wx1 gene is then selected.

In some aspects, in the methods that use a CRISPR-associated nuclease, one guide RNA may be provided. The guide RNA may comprise a variable targeting domain that is complementary to SEQ ID NO:4 [WX-TS1].

In some aspects, in the methods that use a CRISPR-associated nuclease, two guide RNAs may be provided. In one aspect, a first guide RNA may comprise a variable targeting domain that is complementary to SEQ ID NO:1 [WX-TS4] and a second guide RNA may comprise a variable targeting domain that is complementary to SEQ ID NO:2 [WX-TS8]. In another aspect, a first guide RNA may comprise a variable targeting domain that is complementary to SEQ ID NO:1 [WX-TS4] and a second guide RNA may comprise a variable targeting domain that is complementary to SEQ ID NO:9 [WX-TS7]. In another aspect, a first guide RNA may comprise a variable targeting domain that is complementary to SEQ ID NO:1 [WX-TS4] and a second guide RNA may comprise a variable targeting domain that is complementary to SEQ ID NO:8 [WX-TS5]. In another aspect, a first guide RNA may comprise a variable targeting domain that is complementary to SEQ ID NO:7 [WX-TS6]

and a second guide RNA may comprise a variable targeting domain that is complementary to SEQ ID NO:2 [WX-TS8]. In another aspect, a first guide RNA may comprise a variable targeting domain that is complementary to SEQ ID NO:7 [WX-TS6] and a second guide RNA may comprise a variable targeting domain that is complementary to SEQ ID NO:9 [WX-TS7]. In another aspect, a first guide RNA may comprise a variable targeting domain that is complementary to SEQ ID NO:7 [WX-TS6] and a second guide RNA may comprise a variable targeting domain that is complementary to SEQ ID NO:8 [WX-TS5]. In another aspect, a first guide RNA may comprise a variable targeting domain that is complementary to SEQ ID NO:3 [WX-TS10] and a second guide RNA may comprise a variable targeting domain that is complementary to SEQ ID NO:2 [WX-TS8]. In another aspect, a first guide RNA may comprise a variable targeting domain that is complementary to SEQ ID NO:4 [WX-TS1] and a second guide RNA may comprise a variable targeting domain that is complementary to SEQ ID NO: 5 [WX-TS3]. In another aspect, a first guide RNA may comprise a variable targeting domain that is complementary to SEQ ID NO:4 [WX-TS1] and a second guide RNA may comprise a variable targeting domain that is complementary to SEQ ID NO:6 [WX-TS2].

In the methods above, the Cas endonuclease may be a Cas9 endonuclease. A gene encoding the Cas endonuclease may be optimized for maize and/or operably linked to an SV40 nuclear targeting signal upstream of the Cas coding region.

The nucleic acid alteration in the Wx1 nucleotide sequence may be generated in an elite inbred maize plant. In some aspects, the elite inbred maize plant is a member of the Iowa Stiff Stalk Synthetic heterotic group, the non-Stiff Stalk heterotic group, or any other heterotic group known to one of ordinary skill in the art.

Also provided are plants produced by the method and seeds produced by the plants.

A guide polynucleotide molecule comprising a variable targeting domain that is complementary to a target site in the maize Wx1 gene is also provided. The guide polynucleotide may be RNA, DNA, or a combination of RNA and DNA. The guide polynucleotide may have a variable targeting domain that is complementary to SEQ ID NO:1; SEQ ID NO:2; SEQ ID NO:3; SEQ ID NO:4; SEQ ID NO:5; SEQ ID NO:6; SEQ ID NO:7; SEQ ID NO:8; and SEQ ID NO:9.

Methods of producing a Waxy maize hybrid plant are also provided in which an Iowa Stiff Stalk Synthetic maize inbred comprising a nucleic acid alteration that knocks out Wx1 gene function, is crossed with a non-Stiff Stalk maize inbred also comprising a nucleic acid alteration that knocks out Wx1 gene function. The Waxy maize hybrid plant may have similar yield as a maize hybrid plant produced by a cross between the Iowa Stiff Stalk Synthetic maize inbred and the non-Stiff Stalk maize inbred, neither of which have a nucleic acid alteration that knocks out Wx1 gene function.

BRIEF DESCRIPTION OF THE DRAWINGS AND SEQUENCE LISTING

The invention can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

Drawings

FIGS. 1A and 1B show the structure of the Wx1 gene and the strategy for knocking out the function of the gene, respectively. In FIG. 1A, shaded sections indicate exons, and target site locations are indicated by the upside down triangles. In FIG. 1B, the dotted lines indicate deleted sequence.

Figures 2A, 2B:
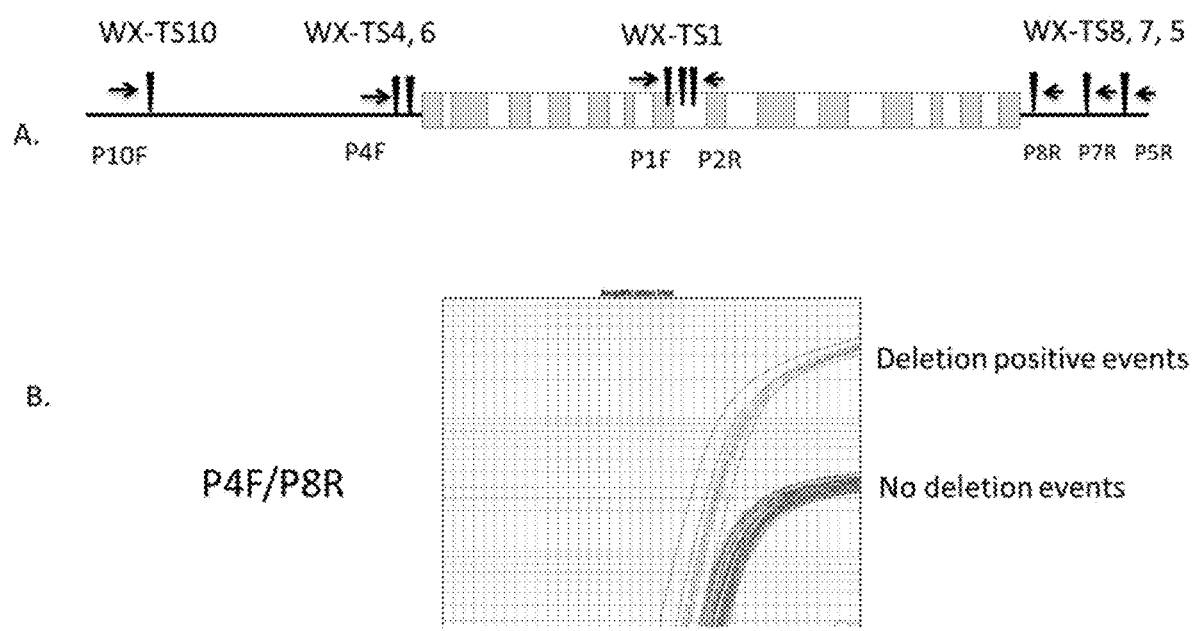

FIGS. 2A and 2B depict screening for Wx1 whole gene deletion events. In FIG. 2A, qPCR primers used for deletion screening are indicated by arrows. Primer pair P4F/P8R was used for deletions generated using the CR4/CR8 or CR6/CR8 pairings. Primer pair P4F/P7R was used for deletions generated using the CR4/CR7 pairing. Primer pair P4F/P5R was used for deletions generated using the CR4/CR5 deletion. Primer pair P10F/P8R was used for deletions generated using the CR10/CR8 deletion. Primer pair P1F/P2R was used for exon 7 and intron junction deletion screening. FIG. 2B shows an amplification plot for CR4/CR8 deletion event screening.

Figure 3:
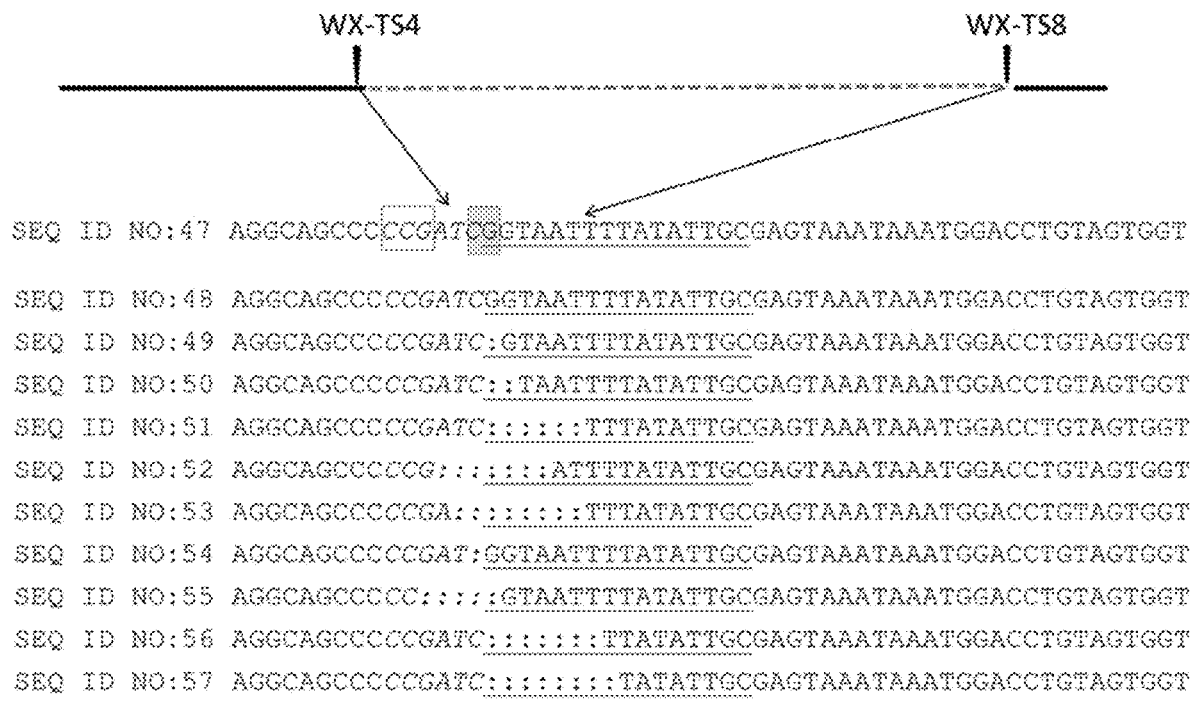

FIG. 3 shows a sequence alignment of generated mutations (SEQ ID NOs:48-57) at the CR4/CR8 deletion junction. SEQ ID NO:47 is the sequence of the wild-type Wx1 gene at the CR4/CR8 junction. The two shaded nucleotides are at the CR4/CR8 junction site; the remaining WX-TS4 target site sequence is in italics; the remaining WX-TS8 sequence is underlined; and the open box indicates the PAM sequence of the remaining target site. Only a sampling of generated mutations at the junction sequence is presented.

Figure 4:

FIG. 4 shows a sequence alignment of generated mutations (SEQ ID NOs: 59-67) at the CR10/CR8 deletion junction. SEQ ID NO:58 is the sequence of the wild-type Waxy gene at the CR10/CR8 junction. The two shaded nucleotides are at the CR10/CR8 junction site; the remaining WX-TS10 target site sequence is in italics; the remaining WX-TS8 sequence is underlined; and the open box indicates the PAM sequence of the remaining target site. Only a sampling of generated mutations at the junction sequence is presented.

FIG. 5 shows a sequence alignment of generated mutations (SEQ ID NOs:69-76) with CR1 only or with CR1/CR3. SEQ ID NO:68 is the sequence of the wild-type Wx1 gene in this region. The WX-TS1 target site is in italics; the WX-TS3 target sit is underlined; and arrows indicate the cleavage sites for WX-TS1 and WX-TS3. Sequences in bold are at the 3'end of exon 7 sequences. The open boxes indicate the PAM sequences. D7-Δ30 bp (SEQ ID NO:69) and the precise CR1/CR3 deletion (SEQ ID NO:75) are also shown. Only a sampling of generated mutations at the junction sequence is presented.

Figure 6A:
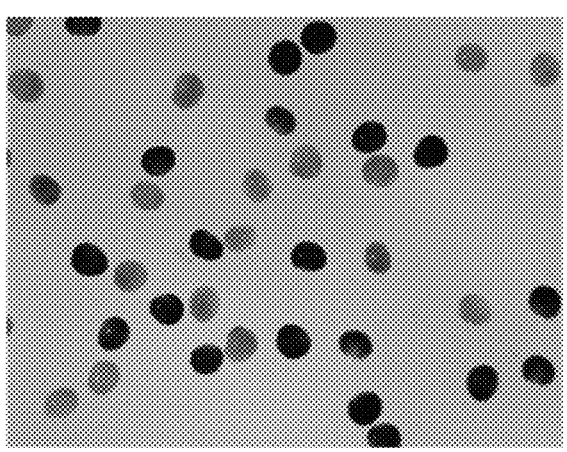
Figure 6B:
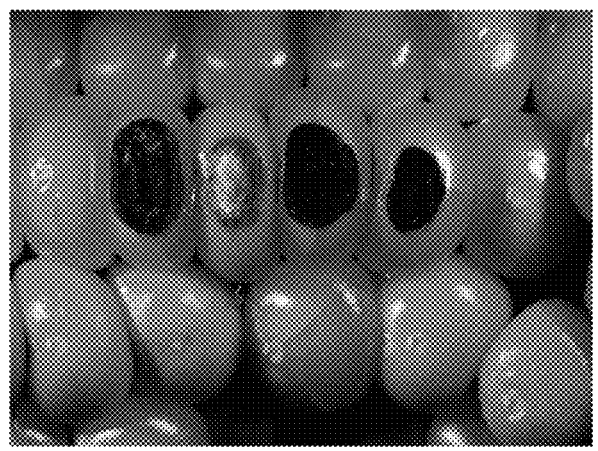

FIGS. 6A and 6B show the Waxy maize phenotype in pollen and kernels, respectively. In FIG. 6A, T0 plants with the CR4/CR8 deletion were stained with iodine. Wild-type pollen having a functional Wx1 gene stained darker blue, while Waxy pollen stained light red color. In FIG. 6B, an ear of maize is shown that has both Waxy kernels (having a Wx1 gene knockout) and normal wild-type kernels (functional Wx1 gene). Waxy (wx1) kernels stain lighter with iodine, while normal wild-type kernels (Wx1) stain darker.

SEQUENCES

SEQ ID NO:1 is the nucleotide sequence of the maize genomic target site WX-TS4.

SEQ ID NO:2 is the nucleotide sequence of the maize genomic target site WX-TS8.

SEQ ID NO:3 is the nucleotide sequence of the maize genomic target site WX-TS10.

SEQ ID NO:4 is the nucleotide sequence of the maize genomic target site WX-TS1.

SEQ ID NO:5 is the nucleotide sequence of the maize genomic target site WX-TS3.

SEQ ID NO:6 is the nucleotide sequence of the maize genomic target site WX-TS2.

SEQ ID NO:7 is the nucleotide sequence of the maize genomic target site WX-TS6.

SEQ ID NO:8 is the nucleotide sequence of the maize genomic target site WX-TS5.

SEQ ID NO:9 is the nucleotide sequence of the maize genomic target site WX-TS7.

SEQ ID NO:10 is the nucleotide sequence of the modified Cas9 gene from *Streptococcus pyogenes* M1 GAS (SF370) with the ST-L1 intron2.

SEQ ID NO:11 is the amino acid sequence of SV40 amino N-terminal.

SEQ ID NO:12 is the nucleotide sequence of the maize U6 polymerase III promoter.

SEQ ID NO:13 is the nucleotide sequence of the WXY-CR4 gRNA expression cassette comprising the maize U6 polymerase III promoter operably linked to the nucleotide variable targeting domain that is complementary to the WXY-TS4 target sequence, followed by an RNA sequence capable of interacting with the double strand break inducing endonuclease.

SEQ ID NO:14 is the nucleotide sequence of the WXY-CR8 gRNA expression cassette comprising the maize U6 polymerase III promoter operably linked to the nucleotide variable targeting domain that is complementary to the WXY-TS8 target sequence, followed by an RNA sequence capable of interacting with the double strand break inducing endonuclease.

SEQ ID NO:15 is the nucleotide sequence of the WXY-CR10 gRNA expression cassette comprising the maize U6 polymerase III promoter operably linked to the nucleotide variable targeting domain that is complementary to the WXY-TS10 target sequence, followed by an RNA sequence capable of interacting with the double strand break inducing endonuclease.

SEQ ID NO:16 is the nucleotide sequence of the WXY-CR1 gRNA expression cassette comprising the maize U6 polymerase III promoter operably linked to the nucleotide variable targeting domain that is complementary to the WXY-TS1 target sequence, followed by an RNA sequence capable of interacting with the double strand break inducing endonuclease.

SEQ ID NO:17 is the nucleotide sequence of the WXY-CR3 gRNA expression cassette comprising the maize U6 polymerase III promoter operably linked to the nucleotide variable targeting domain that is complementary to the WXY-TS3 target sequence, followed by an RNA sequence capable of interacting with the double strand break inducing endonuclease.

SEQ ID NO:18 is the nucleotide sequence of the WXY-CR2 gRNA expression cassette comprising the maize U6 polymerase III promoter operably linked to the nucleotide variable targeting domain that is complementary to the WXY-TS2 target sequence, followed by an RNA sequence capable of interacting with the double strand break inducing endonuclease.

SEQ ID NO:19 is the nucleotide sequence of the WXY-CR6 gRNA expression cassette comprising the maize U6 polymerase III promoter operably linked to the nucleotide variable targeting domain that is complementary to the WXY-TS6 target sequence, followed by an RNA sequence capable of interacting with the double strand break inducing endonuclease.

SEQ ID NO:20 is the nucleotide sequence of the WXY-CR7 gRNA expression cassette comprising the maize U6 polymerase III promoter operably linked to the nucleotide variable targeting domain that is complementary to the WXY-TS7 target sequence, followed by an RNA sequence capable of interacting with the double strand break inducing endonuclease.

SEQ ID NO:21 is the nucleotide sequence of the WXY-CR5 gRNA expression cassette comprising the maize U6 polymerase III promoter operably linked to the nucleotide variable targeting domain that is complementary to the WXY-TS5 target sequence, followed by an RNA sequence capable of interacting with the double strand break inducing endonuclease.

SEQ ID NO:22 is the DNA version of the guide RNA in the WXY-CR4 expression construct.

SEQ ID NO:23 is the DNA version of the guide RNA in the WXY-CR8 expression construct.

SEQ ID NO:24 is the DNA version of the guide RNA in the WXY-CR10 expression construct.

SEQ ID NO:25 is the DNA version of the guide RNA in the WXY-CR1 expression construct.

SEQ ID NO:26 is the DNA version of the guide RNA in the WXY-CR3 expression construct.

SEQ ID NO:27 is the DNA version of the guide RNA in the WXY-CR2 expression construct.

SEQ ID NO:28 is the DNA version of the guide RNA in the WXY-CR6 expression construct.

SEQ ID NO:29 is the DNA version of the guide RNA in the WXY-CR7 DNA expression construct.

SEQ ID NO:30 is the DNA version of the guide RNA in the WXY-CR5 expression construct.

SEQ ID NO:31 is the nucleotide sequence of the P4F forward primer.

SEQ ID NO:32 is the nucleotide sequence of the P8R reverse primer.

SEQ ID NO:33 is the nucleotide sequence of the P7R reverse primer.

SEQ ID NO:34 is the nucleotide sequence of the P5R reverse primer.

SEQ ID NO:35 is the nucleotide sequence of the CR4 probe.

SEQ ID NO:36 is the nucleotide sequence of the P10F forward primer.

SEQ ID NO:37 is the nucleotide sequence of the CR10 probe.

SEQ ID NO:38 is the nucleotide sequence of the NGS 2nd forward primer.

SEQ ID NO:39 is the nucleotide sequence of the NGS 2nd reverse primer.

SEQ ID NO:40 is the nucleotide sequence of the CR4/CR6 mipfl forward primer.

SEQ ID NO:41 is the nucleotide sequence of the CR8mipr reverse primer.

SEQ ID NO:42 is the nucleotide sequence of the CR5mipr reverse primer.

SEQ ID NO:43 is the nucleotide sequence of the CR7mipr reverse primer.

SEQ ID NO:44 is the nucleotide sequence of the CR10mipf forward primer.

SEQ ID NO:45 is the nucleotide sequence of the CR1mipf forward primer.

SEQ ID NO:46 is the nucleotide sequence of the CR1mipr reverse primer.

SEQ ID NO:47 is the nucleotide sequence of the wild-type Waxy gene at the CR4/CR8 junction.

SEQ ID NOs:48-57 are the nucleotide sequences of mutations generated at the CR4/CR8 deletion junction.

SEQ ID NO:58 is the sequence of the wild-type Waxy gene at the CR10/CR8 junction.

SEQ ID NOs: 59-67 are the nucleotide sequences of mutations generated at the CR10/CR8 deletion junction.

SEQ ID NO:68 is the nucleotide sequence of the wild-type Waxy gene in the region containing the TS1 and TS3 target sites.

SEQ ID NOs:69-76 are the nucleotide sequences of mutations generated using CR1 only or CR1/CR3. The D7-Δ30 bp deletion is represented by SEQ ID NO:69, and the precise CR1/CR3 deletion is represented by SEQ ID NO:75.

DETAILED DESCRIPTION

The present disclosure includes the production of maize plants that exhibit the Waxy maize phenotype, i.e. increased amylopectin in pollen and kernels, as compared to a maize plant with a functional Waxy (Wx1) gene. Compositions and methods are provided for knocking out the Wx1 gene in a maize plant cell by introducing double strand breaks (DSBs) at one or more targets sites and optionally providing a polynucleotide modification template.

DSBs can be induced using any DSB-inducing agent available, including, but not limited to, TALENs, meganucleases, zinc finger nucleases, Cas9-gRNA systems (based on bacterial CRISPR-Cas systems), and the like.

TAL effector nucleases (TALEN) are a class of sequence-specific nucleases that can be used to make double-strand breaks at specific target sequences in the genome of a plant or other organism. (Miller et al. (2011) *Nature Biotechnology* 29:143-148).

Meganucleases, also known as homing endonucleases (HEases), are like restriction endonucleases in that they bind and cut at a specific recognition site; however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) *Curr Op Biotechnol* 5:521-7; and Sadowski (1993) *FASEB* 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Some methods presented herein employ one or more guide polynucleotides and Cas endonuclease, wherein a Cas endonuclease is guided by each guide polynucleotide to recognize a target genomic sequence in or around the Wx1 gene and introduce double strand breaks in the target genomic sequence, thereby knocking out the function of the gene.

The term "Cas gene" herein refers to a gene that is generally coupled, associated or close to, or in the vicinity of flanking CRISPR loci in bacterial systems. The terms "Cas gene", "CRISPR-associated (Cas) gene" are used interchangeably herein. The term "Cas endonuclease" herein refers to a protein encoded by a Cas gene. A Cas endonuclease herein, when in complex with a suitable polynucleotide component, is capable of recognizing, binding to, and optionally nicking or cleaving all or part of a specific DNA target sequence. A Cas endonuclease described herein comprises one or more nuclease domains. Cas endonucleases of the disclosure includes those having a HNH or HNH-like nuclease domain and/or a RuvC or RuvC-like nuclease domain. A Cas endonuclease of the disclosure includes a Cas9 protein, a Cpf1 protein, a C2c1 protein, a C2c2 protein, a C2c3 protein, Cas3, Cas 5, Cas7, Cas8, Cas10, or complexes of these.

As used herein, the terms "guide polynucleotide/Cas endonuclease complex", "guide polynucleotide/Cas endonuclease system", "guide polynucleotide/Cas complex", "guide polynucleotide/Cas system", "guided Cas system" are used interchangeably herein and refer to at least one guide polynucleotide and at least one Cas endonuclease that are capable of forming a complex, wherein said guide polynucleotide/Cas endonuclease complex can direct the Cas endonuclease to a DNA target site, enabling the Cas endonuclease to recognize, bind to, and optionally nick or cleave (introduce a single or double strand break) the DNA target site. A guide polynucleotide/Cas endonuclease complex herein can comprise Cas protein(s) and suitable polynucleotide component(s) of any of the four known CRISPR systems (Horvath and Barrangou, 2010, *Science* 327:167-170) such as a type I, II, or III CRISPR system. A Cas endonuclease unwinds the DNA duplex at the target sequence and optionally cleaves at least one DNA strand, as mediated by recognition of the target sequence by a polynucleotide (such as, but not limited to, a crRNA or guide RNA) that is in complex with the Cas protein. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. (See also U.S. Patent Application US 2015-0082478 A1, published on Mar. 19, 2015 and US 2015-0059010 A1, published on Feb. 26, 2015, both are hereby incorporated in its entirety by reference).

A guide polynucleotide/Cas endonuclease complex can cleave one or both strands of a DNA target sequence. A guide polynucleotide/Cas endonuclease complex that can cleave both strands of a DNA target sequence typically comprises a Cas protein that has all of its endonuclease domains in a functional state (e.g., wild type endonuclease domains or variants thereof retaining some or all activity in each endonuclease domain). Thus, a wild type Cas protein (e.g., a Cas9 protein disclosed herein), or a variant thereof retaining some or all activity in each endonuclease domain of the Cas protein, is a suitable example of a Cas endonuclease that can cleave both strands of a DNA target sequence. A Cas9 protein comprising functional RuvC and HNH nuclease domains is an example of a Cas protein that can cleave both strands of a DNA target sequence. A guide polynucleotide/Cas endonuclease complex that can cleave one strand of a DNA target sequence can be characterized herein as having nickase activity (e.g., partial cleaving capability). A Cas nickase typically comprises one functional endonuclease domain that allows the Cas to cleave only one strand (i.e., make a nick) of a DNA target sequence. For example, a Cas9 nickase may comprise (i) a mutant, dysfunctional RuvC domain and (ii) a functional HNH domain (e.g., wild type HNH domain). As another example, a Cas9 nickase may comprise (i) a functional RuvC domain (e.g., wild type RuvC domain) and (ii) a mutant, dysfunctional HNH domain. Non-limiting examples of Cas9 nickases suitable for use herein are disclosed in U.S. Patent Appl. Publ. No. 2014/0189896, which is incorporated herein by reference.

A pair of Cas9 nickases can be used to increase the specificity of DNA targeting. In general, this can be done by providing two Cas9 nickases that, by virtue of being associated with RNA components with different guide sequences, target and nick nearby DNA sequences on opposite strands in the region for desired targeting. Such nearby cleavage of each DNA strand creates a double strand break (i.e., a DSB with single-stranded overhangs), which is then recognized as a substrate for non-homologous-end-joining, NHEJ (prone to imperfect repair leading to mutations) or homologous recombination, HR. Each nick in these embodiments can be at least about 5, 10, 15, 20, 30, 40, 50, 60, 70, 80, 90, or 100 (or any integer between 5 and 100) bases apart from each other, for example. One or two Cas9 nickase proteins herein can be used in a Cas9 nickase pair. For example, a Cas9 nickase with a mutant RuvC domain, but functioning HNH domain (i.e., Cas9 HNH+/RuvC−), could be used (e.g., *Streptococcus pyogenes* Cas9 HNH+/RuvC−). Each Cas9 nickase (e.g., Cas9 HNH+/RuvC−) would be directed to specific DNA sites nearby each other (up to 100 base pairs apart) by using suitable RNA components herein with guide RNA sequences targeting each nickase to each specific DNA site.

A Cas protein can be part of a fusion protein comprising one or more heterologous protein domains (e.g., 1, 2, 3, or more domains in addition to the Cas protein). Such a fusion protein may comprise any additional protein sequence, and optionally a linker sequence between any two domains, such as between Cas and a first heterologous domain. Examples of protein domains that may be fused to a Cas protein herein include, without limitation, epitope tags (e.g., histidine [His], V5, FLAG, influenza hemagglutinin [HA], myc, VSV-G, thioredoxin [Trx]), reporters (e.g., glutathione-5-transferase [GST], horseradish peroxidase [HRP], chloramphenicol acetyltransferase [CAT], beta-galactosidase, beta-glucuronidase [GUS], luciferase, green fluorescent protein [GFP], HcRed, DsRed, cyan fluorescent protein [CFP], yellow fluorescent protein [YFP], blue fluorescent protein [BFP]), and domains having one or more of the following activities: methylase activity, demethylase activity, transcription activation activity (e.g., VP16 or VP64), transcription repression activity, transcription release factor activity, histone modification activity, RNA cleavage activity and nucleic acid binding activity. A Cas protein can also be in fusion with a protein that binds DNA molecules or other molecules, such as maltose binding protein (MBP), S-tag, Lex A DNA binding domain (DBD), GAL4A DNA binding domain, and herpes simplex virus (HSV) VP16.

A Cas protein herein can be from any of the following genera: *Aeropyrum, Pyrobaculum, Sulfolobus, Archaeoglobus, Haloarcula, Methanobacteriumn, Methanococcus, Methanosarcina, Methanopyrus, Pyrococcus, Picrophilus, Thernioplasnia, Corynebacterium, Mycobacterium, Streptomyces, Aquifrx, Porphvromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Streptococcus, Treponema, Francisella,* or *Thermotoga.* See also U.S. patent applications 62/162,377 filed May 15, 2015 and 62/162,353 filed May 15, 2015 (both applications incorporated herein by reference) for more examples of Cas proteins.

A guide polynucleotide/Cas endonuclease complex in certain embodiments can bind to a DNA target site sequence, but does not cleave any strand at the target site sequence. Such a complex may comprise a Cas protein in which all of its nuclease domains are mutant, dysfunctional. For example, a Cas9 protein herein that can bind to a DNA target site sequence, but does not cleave any strand at the target site sequence, may comprise both a mutant, dysfunctional RuvC domain and a mutant, dysfunctional HNH domain. A Cas protein herein that binds, but does not cleave, a target DNA sequence can be used to modulate gene expression, for example, in which case the Cas proteion could be fused with a transcription factor (or portion thereof) (e.g., a repressor or activator, such as any of those disclosed herein). In other aspects, an inactivated Cas protein may be fused with another protein having endonuclease activity, such as a Fok I endonuclease.

The Cas endonuclease gene herein can encode a Type II Cas9 endonuclease, such as but not limited to, Cas9 genes listed in SEQ ID NOs: 462, 474, 489, 494, 499, 505, and 518 of WO2007/025097, published Mar. 1, 2007, and incorporated herein by reference. In another embodiment, the Cas endonuclease gene is a microbe or optimized Cas9 endonuclease gene. The Cas endonuclease gene can be operably linked to a SV40 nuclear targeting signal upstream of the Cas codon region and a bipartite VirD2 nuclear localization signal (Tinland et al. (1992) *Proc. Natl. Acad. Sci. USA* 89:7442-6) downstream of the Cas codon region.

The Cas endonuclease gene includes a plant or microbial codon optimized *Streptococcus pyogenes* Cas9 gene that can recognize any genomic sequence of the form N(12-30)NGG can in principle be targeted or a Cas9 endonuclease originated from an organism selected from the group consisting of *Brevibacillus laterosporus*, *Lactobacillus reuteri* Mlc3, *Lactobacillus rossiae* DSM 15814, *Pediococcus pentosaceus* SL4, *Lactobacillus nodensis* JCM 14932, *Sulfurospirillum* sp. SCADC, *Bifidobacterium thermophilum* DSM 20210, *Loktanella vestfoldensis*, *Sphingomonas sanxanigenens* NX02, *Epilithonimonas tenax* DSM 16811, *Sporocytophaga myxococcoides* and *Psychroflexus torquis* ATCC 700755, wherein said Cas9 endonuclease can form a guide RNA/Cas endonuclease complex capable of recognizing, binding to, and optionally nicking or cleaving all or part of a DNA target sequence. Other Cas endonuclease systems have been described in U.S. patent applications 62/162,377 filed May 15, 2015 and 62/162,353 filed May 15, 2015, both applications incorporated herein by reference.

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises a RuvC nuclease domain and an HNH (H—N—H) nuclease domain, each of which can cleave a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu et al, *Cell* 157:1262-1278). A type II CRISPR system includes a DNA cleavage system utilizing a Cas9 endonuclease in complex with at least one polynucleotide component. For example, a Cas9 can be in complex with a CRISPR RNA (crRNA) and a trans-activating CRISPR RNA (tracrRNA). In another example, a Cas9 can be in complex with a single guide RNA.

The amino acid sequence of a Cas9 protein described herein, as well as certain other Cas proteins herein, may be derived from a *Streptococcus* (e.g., *S. pyogenes*, *S. pneumoniae*, *S. thermophilus*, *S. agalactiae*, *S. parasanguinis*, *S. oralis*, *S. salivarius*, *S. macacae*, *S. dysgalactiae*, *S. anginosus*, *S. constellatus*, *S. pseudoporcinus*, *S. mutans*), *Listeria* (e.g., *L. innocua*), *Spiroplasma* (e.g., *S. apis*, *S. syrphidicola*), *Peptostreptococcaceae*, *Atopobium*, *Porphyromonas* (e.g., *P. catoniae*), *Prevotella* (e.g., *P. intermedia*), *Veillonella*, *Treponema* (e.g., *T. socranskii*, *T. denticola*), *Capnocytophaga*, *Finegoldia* (e.g., *F. magna*), *Coriobacteriaceae* (e.g., *C. bacterium*), *Olsenella* (e.g., *O. profusa*), *Haemophilus* (e.g., *H. sputorum*, *H. pittmaniae*), *Pasteurella* (e.g., *P. bettyae*), *Olivibacter* (e.g., *O. sitiensis*), *Epilithonimonas* (e.g., *E. tenax*), *Mesonia* (e.g., *M. mobilis*), *Lactobacillus* (e.g., *L. plantarum*), *Bacillus* (e.g., *B. cereus*), *Aquimarina* (e.g., *A. muelleri*), *Chryseobacterium* (e.g., *C. palustre*), *Bacteroides* (e.g., *B. graminisolvens*), *Neisseria* (e.g., *N. meningitidis*), *Francisella* (e.g., *F. novicida*), or *Flavobacterium* (e.g., *F. frigidarium*, *F. soli*) species, for example. As another example, a Cas9 protein can be any of the Cas9 proteins disclosed in Chylinski et al. (*RNA Biology* 10:726-737 and U.S. patent application 62/162,377, filed May 15, 2015), which are incorporated herein by reference.

Accordingly, the sequence of a Cas9 protein herein can comprise, for example, any of the Cas9 amino acid sequences disclosed in GenBank Accession Nos. G3ECR1 (*S. thermophilus*), WP_026709422, WP_027202655, WP_027318179, WP_027347504, WP_027376815, WP_027414302, WP_027821588, WP_027886314, WP_027963583, WP_028123848, WP_028298935, Q03JI6 (*S. thermophilus*), EGP66723, EGS38969, EGV05092, EHI65578 (*S. pseudoporcinus*), EIC75614 (*S. oralis*), EID22027 (*S. constellatus*), EIJ69711, EJP22331 (*S. oralis*), EJP26004 (*S. anginosus*), EJP30321, EPZ44001 (*S. pyogenes*), EPZ46028 (*S. pyogenes*), EQL78043 (*S. pyogenes*), EQL78548 (*S. pyogenes*), ERL10511, ERL12345, ERL19088 (*S. pyogenes*), ESA57807 (*S. pyogenes*), ESA59254 (*S. pyogenes*), ESU85303 (*S. pyogenes*), ETS96804, UC75522, EGR87316 (*S. dysgalactiae*), EGS33732, EGV01468 (*S. oralis*), EHJ52063 (*S. macacae*), EID26207 (*S. oralis*), EID33364, EIG27013 (*S. parasanguinis*), EJF37476, EJO19166 (*Streptococcus* sp. BS35b), EJU16049, EJU32481, YP_006298249, ERF61304, ERK04546, ETJ95568 (*S. agalactiae*), TS89875, ETS90967 (*Streptococcus* sp. SR4), ETS92439, EUB27844 (*Streptococcus* sp. BS21), AFJ08616, EUC82735 (*Streptococcus* sp. CM6), EWC92088, EWC94390, EJP25691, YP_008027038, YP_008868573, AGM26527, AHK22391, AHB36273, Q927P4, G3ECR1, or Q99ZW2 (*S. pyogenes*), which are incorporated by reference. A variant of any of these Cas9 protein sequences may be used, but should have specific binding activity, and optionally endonucleolytic activity, toward DNA when associated with an RNA component herein. Such a variant may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference Cas9.

Alternatively, a Cas9 protein may comprise an amino acid sequence that is at least about 80%, 81%, 82%, 83%, 84%, 85%, 86%, 87%, 88%, 89%, 90%, 91%, 92%, 93%, 94%, 95%, 96%, 97%, 98%, or 99% identical to any of the foregoing amino acid sequences, for example. Such a variant Cas9 protein should have specific binding activity, and optionally cleavage or nicking activity, toward DNA when associated with an RNA component herein.

A Cas protein herein such as a Cas9 can comprise a heterologous nuclear localization sequence (NLS). A heterologous NLS amino acid sequence herein may be of sufficient strength to drive accumulation of a Cas protein in a detectable amount in the nucleus of a yeast cell herein, for example. An NLS may comprise one (monopartite) or more (e.g., bipartite) short sequences (e.g., 2 to 20 residues) of basic, positively charged residues (e.g., lysine and/or arginine), and can be located anywhere in a Cas amino acid sequence but such that it is exposed on the protein surface. An NLS may be operably linked to the N-terminus or C-terminus of a Cas protein herein, for example. Two or more NLS sequences can be linked to a Cas protein, for example, such as on both the N- and C-termini of a Cas protein. Non-limiting examples of suitable NLS sequences herein include those disclosed in U.S. Pat. No. 7,309,576, which is incorporated herein by reference.

The Cas endonuclease can comprise a modified form of the Cas9 polypeptide. The modified form of the Cas9 polypeptide can include an amino acid change (e.g., deletion, insertion, or substitution) that reduces the naturally-occurring nuclease activity of the Cas9 protein. For example, in some instances, the modified form of the Cas9 protein has less than 50%, less than 40%, less than 30%, less than 20%, less than 10%, less than 5%, or less than 1% of the nuclease activity of the corresponding wild-type Cas9 polypeptide (US patent application US20140068797 A1, published on Mar. 6, 2014). In some cases, the modified form of the Cas9 polypeptide has no substantial nuclease activity and is referred to as catalytically "inactivated Cas9" or "deactivated cas9 (dCas9)." Catalytically inactivated Cas9 variants include Cas9 variants that contain mutations in the HNH and RuvC nuclease domains. These catalytically inactivated Cas9 variants are capable of interacting with sgRNA and binding to the target site in vivo but cannot cleave either strand of the target DNA.

A catalytically inactive Cas9 can be fused to a heterologous sequence (US patent application US20140068797 A1, published on Mar. 6, 2014). Suitable fusion partners include, but are not limited to, a polypeptide that provides an activity that indirectly increases transcription by acting directly on the target DNA or on a polypeptide (e.g., a histone or other DNA-binding protein) associated with the target DNA. Additional suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity. Further suitable fusion partners include, but are not limited to, a polypeptide that directly provides for increased transcription of the target nucleic acid (e.g., a transcription activator or a fragment thereof, a protein or fragment thereof that recruits a transcription activator, a small molecule/drug-responsive transcription regulator, etc.). A catalytically inactive Cas9 can also be fused to a FokI nuclease to generate double strand breaks (Guilinger et al. 2014. *Nature Biotechnology*, 32(6).

The terms "functional fragment", "fragment that is functionally equivalent" and "functionally equivalent fragment" of a Cas endonuclease are used interchangeably herein, and refer to a portion or subsequence of the Cas endonuclease sequence of the present disclosure in which the ability to recognize, bind to, and optionally nick or cleave (introduce a single or double strand break in) the target site is retained.

The terms "functional variant", "Variant that is functionally equivalent" and "functionally equivalent variant" of a Cas endonuclease are used interchangeably herein, and refer to a variant of the Cas endonuclease of the present disclosure in which the ability to recognize, bind to, and optionally nick or cleave (introduce a single or double strand break in) the target site is retained. Fragments and variants can be obtained via methods such as site-directed mutagenesis and synthetic construction.

Any guided endonuclease can be used in the methods disclosed herein. Such endonucleases include, but are not limited to Cas9 and Cpf1 endonucleases. Many endonucleases have been described to date that can recognize specific PAM sequences (see for example, Jinek et al. 2012. *Science* 337:816-821, U.S. patent applications 62/162,377 filed May 15, 2015 and 62/162,353 filed May 15, 2015 and Zetsche B et al. 2015. *Cell* 163:1013) and cleave the target DNA at a specific positions. It is understood that based on the methods and embodiments described herein utilizing a guided Cas system one can now tailor these methods such that they can utilize any guided endonuclease system.

The endonuclease can be provided to a cell by any method known in the art, for example, but not limited to transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. Uptake of the endonuclease and/or the guided polynucleotide into the cell can be facilitated with a Cell Penetrating Peptide (CPP) as described in U.S. application 62/075,999, filed Nov. 6, 2014.

As used herein, the term "guide polynucleotide", relates to a polynucleotide sequence that can form a complex with a Cas endonuclease and enables the Cas endonuclease to recognize, bind to, and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences. In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. The size of the fragment of the cRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex is a duplexed RNA comprising a duplex crRNA-tracrRNA.

The tracrRNA (trans-activating CRISPR RNA) contains, in the 5'-to-3' direction, (i) a sequence that anneals with the repeat region of CRISPR type II crRNA and (ii) a stem loop-containing portion (Deltcheva et al., *Nature* 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) into the target site. (See also U.S. Patent Application US 2015-0082478 A1, published on Mar. 19, 2015 and US 2015-0059010 A1 published on Feb. 26, 2015, both are hereby incorporated in its entirety by reference.)

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to recognize, bind to, and optionally nick or cleave (introduce a single or double strand break) the target site. (See also U.S. Patent Application US 2015-0082478 A1 published on Mar. 19, 2015 and US 2015-0059010 A1, published on Feb. 26, 2015, both are hereby incorporated in its entirety by reference.)

The term "variable targeting domain" or "VT domain" is used interchangeably herein and includes a nucleotide sequence that can hybridize (is complementary) to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable targeting domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cos endonuclease recognition domain" or "CER domain" (of a guide polynucleotide) is used interchangeably herein and includes a nucleotide sequence that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see for example US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The terms "functional fragment", "fragment that is functionally equivalent" and "functionally equivalent fragment" of a guide RNA, crRNA or tracrRNA are used interchangeably herein, and refer to a portion or subsequence of the guide RNA, crRNA or tracrRNA, respectively, of the present disclosure in which the ability to function as a guide RNA, crRNA or tracrRNA, respectively, is retained.

The terms "functional variant", "Variant that is functionally equivalent" and "functionally equivalent variant" of a guide RNA, crRNA or tracrRNA (respectively) are used interchangeably herein, and refer to a variant of the guide RNA, crRNA or tracrRNA, respectively, of the present disclosure in which the ability to function as a guide RNA, crRNA or tracrRNA, respectively, is retained.

The terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a DNA target site, enabling the Cas endonuclease to recognize, bind to, and optionally nick or cleave (introduce a single or double strand break) the DNA target site. A guide RNA/Cas endonuclease complex herein can comprise Cas protein(s) and suitable RNA component(s) of any of the four known CRISPR systems (Horvath and Barrangou, 2010, Science 327:167-170) such as a type I, II, or III CRISPR system. A guide RNA/Cas endonuclease complex can comprise a Type II Cas9 endonuclease and at least one RNA component (e.g., a crRNA and tracrRNA, or a gRNA). (See also U.S. Patent Application US 2015-0082478 A1, published on Mar. 19, 2015 and US 2015-0059010 A1, published on Feb. 26, 2015, both are hereby incorporated in its entirety by reference).

The guide polynucleotide can be introduced into a cell transiently, as single stranded polynucleotide or a double stranded polynucleotide, using any method known in the art such as, but not limited to, particle bombardment, *Agrobacterium* transformation or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo et al. 2013. *Nucleic Acids Res.* 41: 4336-4343; Ma et al. 2014. *Mol. Ther. Nucleic Acids* 3:e161) as described in U.S. application 62/036,652, filed on Aug. 13, 2014, incorporated herein in its entirety by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one nucleic acid alteration when compared to non-altered target sequence. Such "nucleic acid alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide an guidepolynucleotide/Cas endonuclease complex to a unique DNA target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

Genome editing can be accomplished using any method of gene editing available. For example, gene editing can be accomplished through the introduction into a host cell of a polynucleotide modification template (sometimes also referred to as a gene repair oligonucleotide) containing a targeted modification to a gene within the genome of the host cell. The polynucleotide modification template for use in such methods can be either single-stranded or double-stranded. Examples of such methods are generally described, for example, in US Publication No. 2013/0019349.

In some embodiments, gene editing may be facilitated through the induction of a double-stranded break (DSB) in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), and the like. In some embodiments, the introduction of a DSB can be combined with the introduction of a polynucleotide modification template.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB. Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, U.S. application 62/023,246, filed on Jul. 7, 2014, and U.S. application 62/036,652, filed on Aug. 13, 2014, all of which are incorporated by reference herein.

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

Various methods and compositions can be employed to obtain a cell or organism having a polynucleotide of interest inserted in a target site for a Cas endonuclease. Such methods can employ homologous recombination to provide integration of the polynucleotide of Interest at the target site. In one method provided, a polynucleotide of interest is provided to the organism cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the cell or organism genome. By "homology" is meant DNA sequences that are similar. For example, a "region of homology to a genomic region" that is found on the donor DNA is a region of DNA that has a similar sequence to a given "genomic region" in the cell or organism genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bps. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) *Current Protocols*, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

Polynucleotides of interest and/or traits can be stacked together in a complex trait locus as described in US 2013/0263324-A1, published Oct. 3, 2013 and in PCT/US13/22891, published Jan. 24, 2013, both applications are hereby incorporated by reference. The guide polynucleotide/Cas9 endonuclease system described herein provides for an efficient system to generate double strand breaks and allows for traits to be stacked in a complex trait locus.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the organism genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al. 1982. *Cell* 31:25-33; Shen and Huang. 1986. *Genetics* 112:441-57; Watt et al. 1985. *Proc. Natl. Acad. Sci. USA* 82:4768-72, Sugawara and Haber. 1992. *Mol Cell Biol* 12:563-75, Rubnitz and Subramani. (1984. *Mol Cell Biol* 4:2253-8; Ayares et al. 1986. *Proc. Natl. Acad. Sci. USA* 83:5199-203; Liskay et al. 1987. *Genetics* 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 *Annu. Rev. Biochem.* 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. 2014. *PNAS* (0027-8424), 111 (10), p. E924-E932).

Alteration of the genome of a plant cell, for example, through homologous recombination (HR), is a powerful tool for genetic engineering. Homologous recombination has been demonstrated in plants (Halfter et al. 1992. *Mol Gen Genet* 231:186-93) and insects (Dray and Gloor. 1997. *Genetics* 147:689-99).

Homologous recombination has also been accomplished in other organisms. For example, at least 150-200 bp of homology was required for homologous recombination in the parasitic protozoan *Leishmania* (Papadopoulou and Dumas. 1997. *Nucleic Acids Res* 25:4278-86). In the filamentous fungus *Aspergillus nidulans*, gene replacement has been accomplished with as little as 50 bp flanking homology (Chaveroche et al. 2000. *Nucleic Acids Res* 28:e97). Targeted gene replacement has also been demonstrated in the ciliate *Tetrahymena thermophila* (Gaertig et al. 1994. *Nucleic Acids Res* 22:5391-8). In mammals, homologous recombination has been most successful in the mouse using pluripotent embryonic stem cell lines (ES) that can be grown in culture, transformed, selected and introduced into a mouse embryo (Watson et al., 1992, *Recombinant DNA*, 2nd Ed., (Scientific American Books distributed by WH Freeman & Co.).

Error-prone DNA repair mechanisms can produce mutations at double-strand break sites. The Non-Homologous-End-Joining (NHEJ) pathways are the most common repair mechanism to bring the broken ends together (Bleuyard et al. 2006. *DNA Repair* 5:1-12). The structural integrity of chromosomes is typically preserved by the repair, but deletions, insertions, or other rearrangements are possible. The two ends of one double-strand break are the most prevalent substrates of NHEJ (Kirik et al. 2000. *EMBO J* 19:5562-6), however if two different double-strand breaks occur, the free ends from different breaks can be ligated and result in chromosomal deletions (Siebert and Puchta. 2002. *Plant Cell* 14:1121-31), or chromosomal translocations between different chromosomes (Pacher et al. 2007. *Genetics* 175: 21-9).

Episomal DNA molecules can also be ligated into the double-strand break, for example, integration of T-DNAs into chromosomal double-strand breaks (Chilton and Que. 2003. *Plant Physiol* 133:956-65; Salomon and Puchta. 1998. *EMBO J* 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al. 2004. *Plant Cell* 16:342-52). Ectopic and/or epigenic DNA sequences may also serve as a DNA repair template for homologous recombination (Puchta. 1999. *Genetics* 152: 1173-81).

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) *DNA Repair* 5:1-12). The structural integrity of chromosomes is typically preserved by the repair, but deletions, insertions, or other rearrangements are possible (Siebert and Puchta. 2002. *Plant Cell* 14:1121-31; Pacher et al. 2007. *Genetics* 175:21-9).

Alternatively, the double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) *Plant Cell* 16:342-52). Ectopic and/or epigenic DNA sequences may also serve as a DNA repair template for homologous recombination (Puchta, (1999) *Genetics* 152:1173-81).

DNA double-strand breaks appear to be an effective factor to stimulate homologous recombination pathways (Puchta et al., (1995) *Plant Mol Biol* 28:281-92; Tzfira and White, (2005) *Trends Biotechnol* 23:567-9; Puchta, (2005) *J Exp Bot* 56:1-14). Using DNA-breaking agents, a two- to nine-fold increase of homologous recombination was observed between artificially constructed homologous DNA repeats in plants (Puchta et al., (1995) *Plant Mol Biol* 28:281-92). In maize protoplasts, experiments with linear DNA molecules demonstrated enhanced homologous recombination between plasmids (Lyznik et al., (1991) *Mol Gen Genet* 230:209-18).

The donor DNA may be introduced by any means known in the art. The donor DNA may be provided by any transformation method known in the art including, for example, *Agrobacterium*-mediated transformation or biolistic particle bombardment. The donor DNA may be present transiently in the cell or it could be introduced via a viral replicon. In the presence of the Cas endonuclease and the target site, the donor DNA is inserted into the transformed plant's genome. (see guide language)

Further uses for guide RNA/Cas endonuclease systems have been described (See U.S. Patent Application US 2015-0082478 A1, published on Mar. 19, 2015, WO2015/026886 A1, published on Feb. 26, 2015, US 2015-0059010 A1, published on Feb. 26, 2015, U.S. application 62/023,246, filed on Jul. 7, 2014, and U.S. application 62/036,652, filed on Aug. 13, 2014, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

Knocking Out the Wx1 Gene

Methods for producing Waxy maize plants are provided herein and include obtaining a plant or a seed thereof, wherein the plant or the seed comprises a nucleic acid alteraction in a Wx1 gene that knocks out expression of the gene, the nucleic acid alteration of which is generated by the introduction of one or more double strand breaks using a double strand break inducing agent, and wherein the plant exhibits the Waxy maize phenotype, or grain with an increased percentage of amylopectin compared to a maize plant comprising a functional Wx1 gene.

The double strand breaks are introduced into one or more target sites in an endogenous WX1 encoding sequence in a maize plant cell to produce a maize plant cell with a modified Wx1 nucleotide sequence that includes a nucleic acid alteration that knocks out Wx1 gene function. The double strand break may be induced by a TALEN, a meganuclease, a zinc finger nuclease, a CRISPR-associated nuclease, or any other double strand inducing agent known to one of ordinary skill in the art.

The method may further include introducing a Wx1 polynucleotide modification template in the maize plant cell, in which the Wx1 polynucleotide modification template has at least one nucleic acid alteration (when compared to the endogenous WX1 encoding sequence) that knocks out Wx1 gene function when incorporated into the endogenous WX1 encoding sequence.

In one aspect, the CRISPR/CAS system is used to make double strand breaks at target sites in and around the maize Wx1 gene, and the cell's own repair mechanism joins the ends together. A target site may be any nucleotide sequence in the region of the Wx1 gene (or the endogenous WX1 encoding sequence) that can be targeted for deletion using CRISPR/Cas gene editing technology to generate a loss of function of the Wx1 gene. One or two guide RNAs may be used. If two guide RNAs are used, the intervening sequence is deleted as the gap is repaired by end joining.

A guide RNA may comprise a variable targeting domain that is complementary to SEQ ID NO:1 [WX-TS4], SEQ ID NO:2 [WX-TS8], SEQ ID NO:3 [WX-TS10], SEQ ID NO:4 [WX-TS1], SEQ ID NO: 5 [WX-TS3], SEQ ID NO:6 [WX-TS2], SEQ ID NO:7 [WX-TS6], SEQ ID NO:8 [WX-TS5], or SEQ ID NO:9 [WX-TS7].

Multiple examples of deletions in the Wx1 nucleotide sequence that can be produced via the CRISPR/Cas endonuclease system have been provided herein. The examples include: (1) deletion of whole coding sequences including transcription start sites; (2) deletion of promoter region and coding sequences; and (3) generation of frame shifts such as but not limited to a frame shift with a small deletion or extended sequence deletion at the exon 7/intron junction. However, the CRISPR-Cas endonuclease system can be used to introduce any deletion that results in the loss of Waxy gene function.

CRISPR-Cas gene editing technology allows mutations in the Waxy gene to be directly introduced into higher yielding elite inbreds in order to create commercial hybrids in the next immediate step. The inbred may be from the Iowa Stiff Stalk Synthetic heterotic group, the non-Stiff Stalk heterotic group, or any other heterotic group known to one of ordinary skill in the art.

A "heterotic group" comprises a set of genotypes that perform well when crossed with genotypes from a different heterotic group (Hallauer et al. (1998) *Corn breeding*, p. 463-564. In G. F. Sprague and J. W. Dudley (ed.) Corn and corn improvement). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Cornbelt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci:* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

Maize hybrids may be created by crossing an Iowa Stiff Stalk Synthetic inbred plant with a non-Stiff Stalk inbred plant. Mutations that result in a loss of function of the Wx1 gene are recessive; hence, a loss of function allele (whether the same or different) must be present in each of the inbred parents to generate a hybrid maize plant with the Waxy phenotype. Introducing a loss of function allele into each inbred parent eliminates the need for multiple cycles of breeding to produce a Waxy maize commercial product. Moreover, the methods described herein break the linkage with genetic material that has a negative impact on the plant, such as for example, on yield. Hence, when a Waxy maize hybrid plant produced by crossing a male inbred with a female inbred, wherein both comprise a loss of function allele of the Wx1 gene, is compared to a wild-type maize plant produced by genetically similar inbred parents, except the parents do not have loss of function alleles at the Wx1 gene, no significant difference in yield should be observed.

Moreover, segregation as part of the breeding process eliminates all other foreign genetic elements, making the process akin to natural mutagenesis.

"Maize" refers to a plant of the *Zea mays* L. ssp. *mays* and is also known as "corn". These terms are used interchangeably herein.

EXAMPLES

In the following Examples, unless otherwise stated, in which parts and percentages are by weight and degrees are Celsius. It should be understood that these Examples, while indicating embodiments of the invention, are given by way of illustration only. From the above discussion and these Examples, one skilled in the art, can make various changes and modifications of the invention to adapt it to various usages and conditions. Such modifications are also intended to fall within the scope of the appended embodiments.

Example 1

Knocking Out the Wx1 Gene in Maize Elite Lines: Target Site Selection and Cas9 and Guide RNA Vector Construction Target Site Selection The gRNA/Cas9 Site directed nuclease system, described in WO2015026885, WO20158026887, WO2015026883, and WO2015026886, was used to knock out the Waxy gene in maize. The following pairs of target sites were used for deletion of the entire Waxy coding sequence: WX-TS4 with WX-TS8; WX-TS4 with WX-TS7; WX-TS4 with WX-TS5; WX-TS6 with WX-TS8; WX-TS6 with WX-TS7; and WX-TS6 with WX-TS5. The paired target sites WX-TS10 and WX-TS8 were used for promoter and coding sequence deletion, and WX-TS1 was used alone or paired with WX-TS3 or WX-TS2 for frame shift deletions in the exon 7 and subsequent intron region. Most target site sequences were conserved in all the inbred lines used except WX-TS7 which was only present in one line. The location of each target site in the Waxy genomic sequence is shown in FIG. 1A, and the target sequences are listed in Table 1. FIG. 1B also shows a schematic drawing of the mutation types.

TABLE 1

Maize Wx1 genomic target site sequences

| Target Site Designation | Maize Genomic Target Site Sequence | PAM Sequence | SEQ ID NO: |
|---|---|---|---|
| WX-TS4 | GCCCAAAACGCTTTCCCGAT | CGG | 1 |
| WX-TS8 | GCAATATAAAATTACCGAT | CGG | 2 |
| WX-TS10 | GCTGGGAGAGACGGTGTAGTA | GGG | 3 |
| WX-TS1 | GGCATCTACAGGGACGCAA | AGG | 4 |
| WX-TS3 | GAGCATGGAGAACGAAGA | CGG | 5 |

TABLE 1 -continued

Maize Wx1 genomic target site sequences

| Target Site Designation | Maize Genomic Target Site Sequence | PAM Sequence | SEQ ID NO: |
|---|---|---|---|
| WX-TS2 | GCTCGTATATACCTCGTC | TGG | 6 |
| WX-TS6 | GCTGGTGCGCAGTGCCGG | GGG | 7 |
| WX-TS5 | GACAATGCCCTAAATATCTAT | AGG | 8 |
| WX-TS7 | GAGACCATAGCCTATCTT | TGG | 9 |

Cas9 Vector Construction

The Cas9 gene from *Streptococcus pyogenes* M1 GAS (SF370) (SEQ ID NO:10) was maize codon optimized per standard techniques known in the art and the potato ST-LS1 intron was introduced in order to eliminate its expression in *E. coli* and *Agrobacterium*. To facilitate nuclear localization of the Cas9 protein in maize cells, Simian virus 40 (SV40) monopartite amino terminal nuclear localization signal (MAPKKKRKVH, SEQ ID NO:11) was incorporated at the amino terminus of the Cas9 open reading frame. The maize optimized Cas9 gene was operably linked to a maize Ubiquitin promoter using standard molecular biological techniques.

Guide RNA Vector Construction

To direct Cas9 nuclease to the designated genomic target sites (Table 1), a maize U6 polymerase III promoter (SEQ ID NO:12; see WO2015026885, WO20158026887, WO2015026883, and WO2015026886) and its cognate U6 polymerase III termination sequences (TTTTTTTT) were used to direct initiation and termination of gRNA expression. Guide RNA variable targeting domains for Waxy gene mutagenesis are identified as WXY-CR1, WXY-CR2, WXY-CR3, WXY-CR4, WXY-CR5, WXY-CR6, WXY-CR7, WXY-CR8, and WXY-CR10, which correspond to the genomic target sites WX-TS1, WX-TS2, WX-TS3, WX-TS4, WX-TS5, WX-TS6, WX-TS7, WX-TS8, and WX-TS10, respectively. DNA encoding each of the variable nucleotide targeting domains was cloned into a gRNA expression cassette through BsbI sites using double strand oligos. Each guide RNA expression cassette (Table 2) thus consists of the U6 polymerase III maize promoter operably linked to the DNA version of the guide RNA, which consists of the respective nucleotide variable targeting domain followed by a polynucleotide sequence capable of interacting with the double strand break inducing endonuclease, and then the cognate U6 polymerase III termination sequence.

TABLE 2

Guide RNA Expression Cassettes

| Name | Guide RNA expression cassette SEQ ID NO: | DNA version of guide RNA SEQ ID NO: |
|---|---|---|
| WXY-CR4 | 13 | 22 |
| WXY-CR8 | 14 | 23 |
| WXY-CR10 | 15 | 24 |
| WXY-CR1 | 16 | 25 |
| WXY-CR3 | 17 | 26 |
| WXY-CR2 | 18 | 27 |
| WXY-CR6 | 19 | 28 |
| WXY-CR7 | 20 | 29 |
| WXY-CR5 | 21 | 30 |

Example 2

Delivery of the Guide RNA/Cas9 Endonuclease System DNA to Maize

Plasmids containing the Cas9 and guide RNA expression cassettes described above were co-bombarded with plasmids containing the transformation selectable marker NPTII and the transformation enhancing developmental genes ODP2 (AP2 domain transcription factor ODP2 (Ovule development protein 2)) and Wuschel into elite maize lines' genomes. Transformation of maize immature embryos can be performed using any method known in the art or the method described below.

In one transformation method, ears are husked and surface sterilized in 30-50% Clorox bleach plus 0.5% Micro detergent for 10 minutes and then rinsed two times with sterile water. The immature embryos are isolated and placed embryo axis side down (scutellum side up), with 25 embryos per plate, on 13224E medium for 2-4 hours and then aligned within the 2.5-cm target zone in preparation for bombardment.

DNA of plasmids is adhered to 0.6 µm (average diameter) gold pellets using a proprietary lipid-polymer mixture of TransIT®-2020 (Cat #MIR 5404, Mirus Bio LLC, Madison, Wis. 5371). DNA solution was prepared using 1 µg of plasmid DNA and optionally, other constructs were prepared for co-bombardment using 10 ng (0.5 µl) of each plasmid. To the pre-mixed DNA, 50 µl of prepared gold particles (30 mg/ml) and 1 µl TransIT®-2020 are added and mixed carefully. The final mixture is allowed to incubate under constant vortexing at low speed for 10 minutes. After the precipitation period, the tubes are centrifuged briefly, and liquid is removed. Gold particles are pelleted in a microfuge at 10,000 rpm for 1 min, and aqueous supernatant is removed. 120 µl of 100% EtOH is added, and the particles are resuspended by brief sonication. Then, 10 µl is spotted on to the center of each macrocarrier and allowed to dry about 2 minutes before bombardment, with a total of ten aliquots taken from each tube of prepared particles/DNA.

The sample plates are bombarded with a Biolistic PDA-1000/He (Bio-Rad). Embryos are 6 cm from the macrocarrier, with a gap of 1/8$^{th}$ of an inch between the 200 psi rupture disc and the macrocarrier. All samples receive a single shot.

Following bombardment, the embryos are incubated on the bombardment plate for ~20 hours then transferred to 13266L (rest/induction medium) for 7-9 days at temperatures ranging from 26-30° C. Embryos are then transferred to the maturation media 289H for ~21 days. Mature somatic embryos are then transferred to germination media 272G and moved to the light. In about 1 to 2 weeks plantlets containing viable shoots and roots are sampled for analysis and sent to the greenhouse where they are transferred to flats (equivalent to a 2.5" pot) containing potting soil. After 1-2 weeks, the plants are transferred to Classic 600 pots (1.6 gallon) and grown to maturity.

Media:

Bombardment medium (13224E) comprises 4.0 g/l N6 basal salts (SIGMA C-1416), 1.0 ml/l Eriksson's Vitamin Mix (1000× SIGMA-1511), 0.5 mg/l thiamine HCl, 190.0 g/l sucrose, 1.0 mg/l 2,4-D, and 2.88 g/l L-proline (brought to volume with D-I H2O following adjustment to pH 5.8 with KOH); 6.3 g/l Sigma agar (added after bringing to volume with D-I H2O); and 8.5 mg/l silver nitrate (added after sterilizing the medium and cooling to room temperature).

Selection medium (13266L) comprises 1650 mg/l ammonium Nitrate, 277.8 mg/l ammonium Sulfate, 5278 mg/l potassium nitrate, calcium chloride, anhydrous 407.4 mg/l calcium chloride, anhydrous, 234.92 mg/l magnesium sulfate, anhydrous, 410 mg/l potassium phosphate, monobasic, 8 mg/l boric acid, 8.6 mg/l, zinc sulfate.7h2o, 1.28 mg/l potassium iodide, 44.54 mg/l ferrous sulfate.7h2o, 59.46 mg/l na2edta.2h2o, 0.025 mg/l cobalt chloride.6h2o, 0.4 mg/l molybdic acid (sodium salt).2h2o, 0.025 mg/l cupric sulfate.5h2o, 6 mg/l manganese sulfate monohydrate, 2 mg/l thiamine, 0.6 ml/l b5h minor salts 1000×, 0.4 ml/l eriksson's vitamins 1000×, 6 ml/l s&h vitamin stock 100×, 1.98 g/l 1-proline, 3.4 mg/l silver nitrate, 0.3 g/l casein hydrolysate (acid), 20 g/l sucrose, 0.6 g/l glucose, 0.8 mg/l 2,4-d, 1.2 mg/l dicamba, 6 g/l tc agar, 100 mg/l agribio carbenicillin, 25 mg/l cefotaxime, and 150 mg/l geneticin (g418)

Plant regeneration medium (289H) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 8.0 g/l Sigma agar (added after bringing to volume with D-I H2O); and 1.0 mg/l indoleacetic acid and 150 mg/l Geneticin (G418) (added after sterilizing the medium and cooling to 60° C.).

Hormone-free medium (272G) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 0.5 mg/l IBA and 150 mg/l Geneticin (G418) and 6 g/l bacto-agar (added after bringing to volume with polished D-I H2O), sterilized and cooled to 60° C.

Example 3

Screening of T0 Plants and Event Characterization

To identify whole Wx1 gene deletion positive events, genomic DNA was extracted from leaf tissue of T0 plants, and qPCR was performed using QuantiTect Mulitplex qPCR Kit (QIAGEN, CAT no. 204545) and the primers listed in Table 3. Primer locations are shown in FIG. 2A. Amplicons obtained when the CR4/CR8, CR4/CR5, CR4/CR7, CR6/CR8, CR6/CR5, CR6/CR7 or CR10/CR8 were cleaved and ligated together after the sequence (3.8 kb-6.2 kb) between the two sites was deleted were removed from the screening process. As an example, FIG. 3 shows a sequence alignment of generated mutations at the CR4/CR8 deletion junction; and FIG. 4 shows a sequence alignment of generated mutations at the CR10/CR8 junction. FIGS. 3 and 4 show a small sample of the generated mutations that were obtained.

Next Generation Sequencing (NGS) was used to evaluate the junction sequences in the deletion qPCR positive events. The junction was PCR amplified with PHUSION® Flash High Fidelity PCR Master Mix (New England Biolabs, F-548). The primers used in the primary PCR reaction are shown in Table 4 and the primers used in the secondary PCR reaction are:

```
                                  (forward, SEQ ID NO: 38)
AATGATACGGCGACCACCGAGATCTACACATACGAGATCCGTAatcggga agctgaag
and
                                  (reverse, SEQ ID NO: 39)
CAAGCAGAAGACGGCATACGAGATNNNNNNNNACACGCACGatccgacgg tagtgt.
```

NNNNNNNN are the barcode sequences corresponding to sample locations on a plate.

TABLE 3

Primers used to screen for Wx1 whole gene deletions

| Name of deletion | Primer name | Primer Orientation | Primary PCR Primer Sequence | SEQ ID NO: |
|---|---|---|---|---|
| CR4(CR6)/ CR8 (CR7 or CR5) | P4F | Forward | GTGTGCGTGC GTGCAGAC | 31 |
| | P8R | Reverse | AGCAGGGATTATTTACTCC ACCAC | 32 |
| | P7R | Reverse | GCCAGAAGCTGCCAGAAGC | 33 |
| | P5R | Reverse | GCTAAATGTAGGTGAATGA AACAAGAA | 34 |
| | CR4 probe | | CAAGCCAAGGCGAGG | 35 |
| CR10-CR8 | P10F | Forward | CATATGGAGAGGTTAAGAC AGCAATT | 36 |
| | P8R | Reverse | AGCAGGGATTATTTACTCC ACCAC | 32 |
| | CR10 probe | | AATTTGATGCCGTCCTAT | 37 |

TABLE 4

NGS first PCR primers

| Name | Primer Orientation | Primary PCR Primer Sequence | SEQ ID NO: |
|---|---|---|---|
| CR4/CR6 mipf1 | Forward | atcgggaagctgaagTGCGTGCGT GCAGACGACAA | 40 |
| CR8 mipr | Reverse | atccgacggtagtgtGAGGAGCGA TAAGAACACCGAACA | 41 |
| CR5 mipr | Reverse | atccgacggtagtgtAAATGTAGG TGAATSAAACAAGAAAC | 42 |
| CR7 mipr | Reverse | atccgacggtagtgtGGATCTAGA AAGTGACAGATTCCTAATATTACA | 43 |
| CR10 mipf | Forward | atcgggaagctgaagGGTTAAGAC AGCAATTAATTTGATGCC | 44 |
| CR1 mipf | Forward | atcgggaagctgaagGCCCTCTCT CGTGCTACCTCA | 45 |
| CR1 mipr | Reverse | atccgacggtagtgtGAAGATGGT CAGACAGACATGCAGT | 46 |

Note:
CR4/CR6mipf1 will combine with reverse primers CR8, CR5, and CR7; CR10 mipf also combined with CR8 reverse primer.

Events containing a frameshift in Wx1 at exon 7, generated using guide RNA CR1, CR1/CR3, or CR1/CR2, were evaluated by NGS only due to a high mutation frequency (~80%). T0 plants were selected based on sequence analysis (FIG. 5 shows a representation of deletions in the WX-TS1 region). The pairings of CR4/CR5, CR4/CR7, CR6/CR8, CR6/CR7, and CR6/CR5 generated deletions in Waxy in two transformed inbred lines. The CR4/CR8 and CR10/CR8 were used in more inbreds, and deletion events were obtained in most of them. A range of deletions (nucleotide insertions) were observed at the CR1 site. Moreover, a WX-D7□30 bp mutant which mimicked the natural mutant (China waxy) was generated in 2 inbred lines when CR1/CR3 guide RNAs were used.

T1 Analysis

T0 plants harboring the created wx1 alleles were transferred to a controlled environment. Pollen from (Wx1/wx1) T0 plants was carried to recurrent parent plants to produce seed. Some pollen from the T0 plants was stained with potassium iodide solution (Lugol, Sigma 62650). FIG. 6A shows wild-type Wx1 pollen (darker stained) compared to the generated mutant wx1 pollen (lighter stained).

T1 plants went through more comprehensive molecular characterization to not only confirm that mutations observed in T0 plant were stably inherited but also to verify that the T1 or later generation plants were free from any foreign DNA elements used during the transformation process. First, qPCR was performed on all helper genes including Cas9, the guide RNAs, the transformation selection marker (NPTII), and the transformation enhancing genes ODP2 and WUS2 to make sure the genes segregated away from the generated wx1 mutant alleles. Then the T1 plants were sampled using Southern by Sequencing (SbS) analysis to further demonstrate that the plants are free of any foreign DNA (Zastron-Hayes et al. 2015. *The Plant Genome* 8. doi:10.3835/plantgenome2014.08.0037).

$BC_0F_2$ (selfed T1) seeds showed segregating Waxy maize kernels (FIG. 6B) amongst normal kernels on an ear. A 3 normal kernel:1 Waxy kernel segregation pattern was observed.

In flours ground from separated $BC_1F_2$ segregating material (T3 seed), a Megazyme kit was used to determine amylose vs. amylopectin ratios (Table 5). The results showed no significant differences in Waxy amylopectin % between example inbreds generated using CRISPR/CAS system (EMTA.2015.G091.2.5 & EMTA.2015.G093.1.6), compared to its equivalent inbreds generated by conventional introgression breeding (PH184CWX1 Check1 and Check2). The Megazyme kit is the industry standard for amylose/amylopectin determinations in cereal flours, based on the method described in Yun, S. H. and Matheson, N. K. 1990. *Starch/Starke* 42:302-305. Similar confirmations of amylose/amylopectin determinations can be conducted on additional inbred or hybrid material.

TABLE 5

Mean Amylopectin % in BC1F2 grain flours from CRISPR/Cas-derived Waxy inbreds versus conventional Waxy inbred checks.

| Lab | Trait | Event_Name | bygroup | Letter Group | ADJUSTMENT | mean | Lower_Mean | Upper_Mean | Low (sub) | Upp (add) |
|---|---|---|---|---|---|---|---|---|---|---|
| EPL | WAXY | EMTA.2015.G091.2.5 | 1 | a | LSD(P < 0.05) | 91.68 | 88.53 | 94.36 | 3.14 | 2.68 |
| EPL | WAXY | EMTA.2015.G093.1.6 | 1 | a | LSD(P < 0.05) | 92.05 | 89.16 | 94.53 | 2.89 | 2.48 |
| EPL | WAXY | PH184CWX1 CHECK1 | 1 | a | LSD(P < 0.05) | 94.15 | 88.82 | 97.83 | 5.32 | 3.68 |
| EPL | WAXY | PH184CWX1 CHECK2 | 1 | a | LSD(P < 0.05) | 92.90 | 88.87 | 96.07 | 4.03 | 3.18 |
| EPL | WT | EMTA.2015.G091.2.5 | 1 | b | LSD(P < 0.05) | 77.61 | 71.68 | 83.02 | 5.93 | 5.42 |
| EPL | WT | EMTA.2015.G093.1.6 | 1 | b | LSD(P < 0.05) | 78.84 | 73.02 | 84.13 | 5.83 | 5.29 |
| EPL | WT | PH184C CHECK1 | 1 | b | LSD(P < 0.05) | 78.62 | 71.73 | 84.78 | 6.89 | 6.16 |
| PHI | WAXY | EMTA.2015.G091.2.5 | 2 | a | LSD(P < 0.05) | 93.73 | 92.22 | 95.08 | 1.50 | 1.35 |
| PHI | WAXY | EMTA.2015.G093.1.6 | 2 | a | LSD(P < 0.05) | 94.78 | 93.40 | 96.01 | 1.39 | 1.23 |
| PHI | WAXY | PH184CWX1 CHECK2 | 2 | a | LSD(P < 0.05) | 94.20 | 92.10 | 95.99 | 2.10 | 1.79 |
| PHI | WAXY | PH184CWX1 CHECK1 | 2 | b | LSD(P < 0.05) | 90.45 | 87.87 | 92.76 | 2.58 | 2.30 |
| PHI | WT | EMTA.2015.G091.2.5 | 2 | c | LSD(P < 0.05) | 77.26 | 74.75 | 79.68 | 2.51 | 2.42 |
| PHI | WT | EMTA.2015.G093.1.6 | 2 | c | LSD(P < 0.05) | 76.43 | 73.88 | 78.88 | 2.54 | 2.45 |
| PHI | WT | PH184C CHECK1 | 2 | c | LSD(P < 0.05) | 73.21 | 69.44 | 76.81 | 3.77 | 3.60 |

What is claimed is:

1. A method for obtaining a Waxy maize plant, the method comprising:
   a) introducing a double-strand break by a Cas endonuclease to at least one target site in an endogenous WX1 encoding sequence in a maize plant cell to produce a maize plant cell with a modified Wx1 nucleotide sequence, wherein the modified Wx1 nucleotide sequence comprises a nucleic acid alteration that creates a deletion event at exon 7 of the Wx1 nucleotide sequence that knocks out Wx1 gene function; and
   b) generating a maize plant from the maize plant cell of (a), wherein said maize plant produces grain with an increased percentage of amylopectin compared to a second maize plant comprising a functional Wx1 gene.

2. The method of claim 1, further comprising introducing a Wx1 polynucleotide modification template in the maize plant cell, wherein said Wx1 polynucleotide modification template comprises at least one nucleic acid alteration that knocks out Wx1 gene function and said Wx1 polynucleotide modification template is incorporated into the endogenous WX1 encoding sequence.

3. The method of claim 1, wherein said double-strand break is induced by a CRISPR-associated nuclease and wherein a guide RNA is provided.

4. The method of claim 3, wherein said guide RNA comprises a variable targeting domain that is complementary to SEQ ID NO:1 [WX-TS4].

5. The method of claim 1, wherein a pair of guide RNAs are provided.

6. The method of claim 5, wherein said pair of guide RNAs comprises:
   a. a first guide RNA comprising a variable targeting domain that is complementary to SEQ ID NO:1 [WX- TS4] and a second guide RNA comprising a variable targeting domain that is complementary to SEQ ID NO:2 [WX-TS8];
  b. a first guide RNA comprising a variable targeting domain that is complementary to SEQ ID NO:1 [WX-TS4] and a second guide RNA comprising a variable targeting domain that is complementary to SEQ ID NO:9 [WX-TS7]; or
  c. a first guide RNA comprising a variable targeting domain that is complementary to SEQ ID NO:1 [WX-TS4] and a second guide RNA comprising a variable targeting domain that is complementary to SEQ ID NO:8 [WX-T55].

7. The method of claim 1, wherein said Cas endonuclease is a Cas9 endonuclease.

8. The method of claim 1, wherein a gene encoding the Cas endonuclease is optimized for maize.

9. The method of claim 1, wherein a gene encoding the Cas endonuclease is operably linked to an SV40 nuclear targeting signal upstream of the Cas coding region.

10. The method of claim 1, wherein the nucleic acid alteration occurs in an elite inbred maize plant.

11. A plant produced by the method of claim 1.

12. Seed produced by the plant of claim 11.

\* \* \* \* \*